United States Patent [19]

Wielopolski et al.

[11] Patent Number: 5,142,559
[45] Date of Patent: Aug. 25, 1992

[54] RADIATION DETECTION SYSTEM INCLUDING RADIATION ALIGNMENT MEANS AND ISOCENTRICALLY ROTATABLE DETECTORS

[75] Inventors: Lucian Wielopolski, Shirley, N.Y.; Israel Waldman, Haifa, Israel

[73] Assignee: The Research Foundation of State University of New York, Albany, N.Y.

[21] Appl. No.: 522,222

[22] Filed: May 11, 1990

[51] Int. Cl.$^5$ .............................................. A61B 6/08
[52] U.S. Cl. ................................. 378/205; 378/19; 378/62; 378/163; 378/164; 378/206; 378/65; 358/111; 250/492.3
[58] Field of Search ................... 378/20, 65, 205, 901, 378/206, 193, 207, 19, 62, 197, 189, 190, 146, 163, 164, 197.4, 196, 99; 358/111; 250/492.3, 252.1, 385, 385.1

[56] References Cited

U.S. PATENT DOCUMENTS

| | | | |
|---|---|---|---|
| 3,783,251 | 1/1974 | Pavkovich | 378/65 |
| 3,991,310 | 11/1976 | Morrison | 378/65 |
| 4,118,631 | 10/1978 | Froggatt | 378/65 |
| 4,123,660 | 10/1978 | Horwitz | 378/65 |
| 4,223,227 | 9/1980 | Horwitz | 378/65 |
| 4,256,966 | 3/1981 | Heinz | 378/65 |
| 4,296,329 | 10/1981 | Mirabella | 378/206 |
| 4,365,341 | 12/1982 | Lam | 378/65 |
| 4,426,351 | 1/1984 | Leboutet | 378/206 |
| 4,426,726 | 1/1984 | Cheetham | 378/206 |
| 4,538,289 | 8/1985 | Scheibengraber | 378/20 |
| 4,628,523 | 12/1986 | Heflin | 378/193 |
| 4,697,280 | 9/1987 | Zarnstorff et al. | 378/207 |
| 4,908,843 | 3/1990 | Gall et al. | 378/99 |
| 4,917,344 | 4/1990 | Prechter et al. | 250/492.3 |
| 4,987,585 | 1/1991 | Kidd et al. | 378/197 |
| 4,988,866 | 1/1991 | Westerlund | 250/252.1 |
| 4,995,068 | 2/1991 | Chou et al. | 378/189 |

Primary Examiner—Janice A. Howell
Assistant Examiner—Kim-Kwok Chu
Attorney, Agent, or Firm—Hoffmann & Baron

[57] ABSTRACT

An assembly is provided which is capable of the multiple functions that are necessary for the quality control of teleradiotherapy machines such a high energy medical accelerators, cobalt 60 machines, and low energy x-ray machines. The assembly includes a detector which is isocentrically rotatable about a pair of horizontal axes. Photodetectors or a luminescent screen are provided within the detector for detecting light and/or radiation. Tests which may be performed with the assembly include determining the position and size of a light field, the mechanical isocentricity of the gantry and of the collimator, positioning of the lasers in the treatment room, the optical distance indicator, and coincidence, symmetry, flatness and uniformity of the radiation and light fields. The multifunctionality of the assembly is based upon the isocentricity of the detector, this invariant point in space being positioned to coincide with that of the treatment machine. A video system may be interfaced to an image processing unit to facilitate observation of the detector during its use and to perform analysis, recording and documenting.

42 Claims, 26 Drawing Sheets

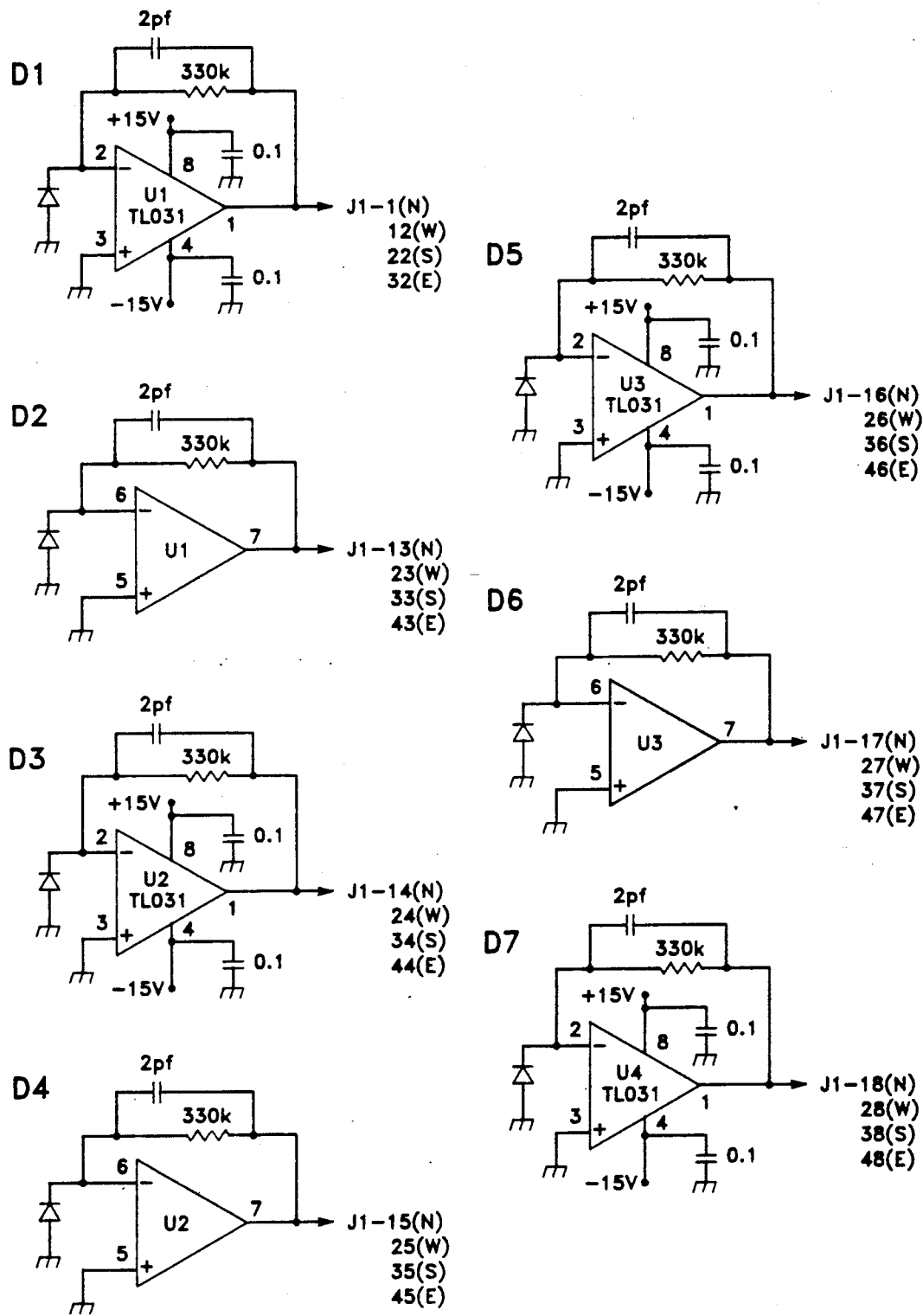
FIG-6a EDGE PREAMPS

FIG-6b  LASER PREAMPS
D RIGHT
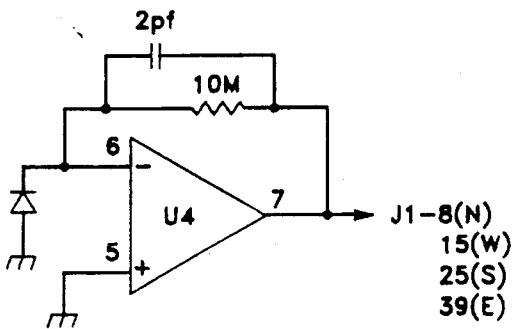
D MIDDLE
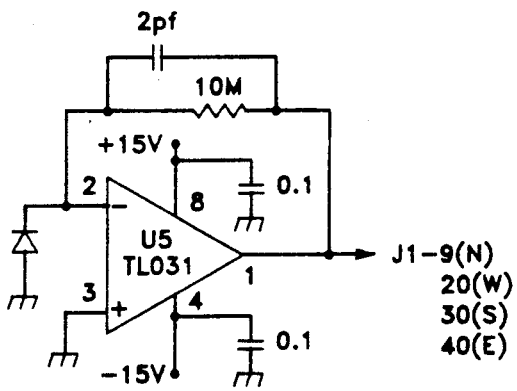
D LEFT
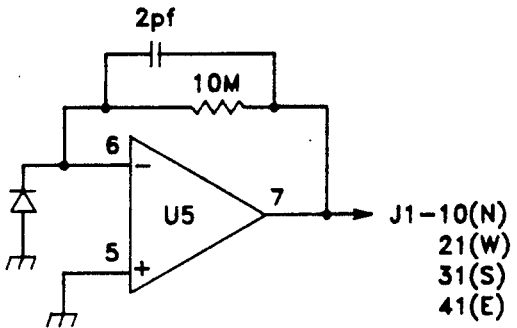

FIG-6c REFERENCE PREAMP
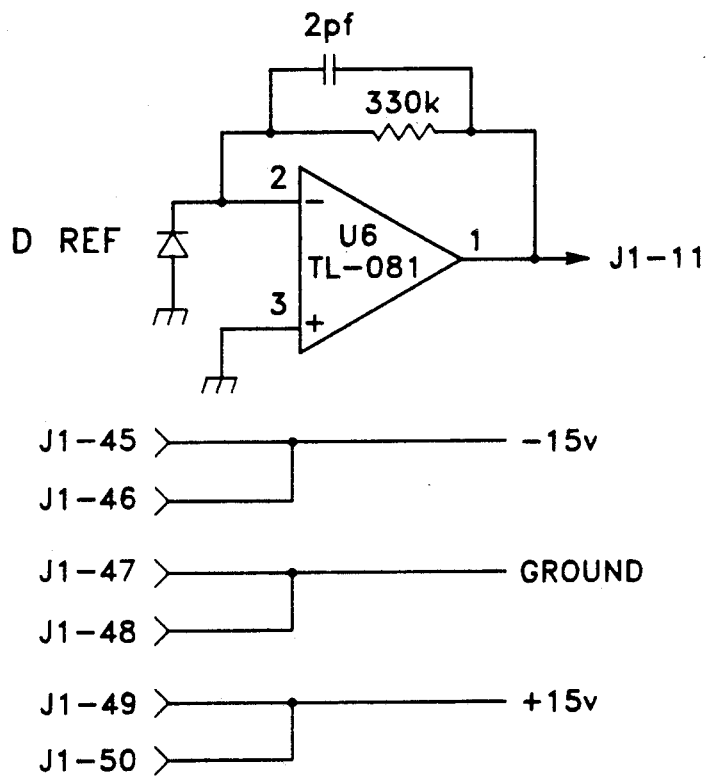
FIG-7 DISPLAY PLATE
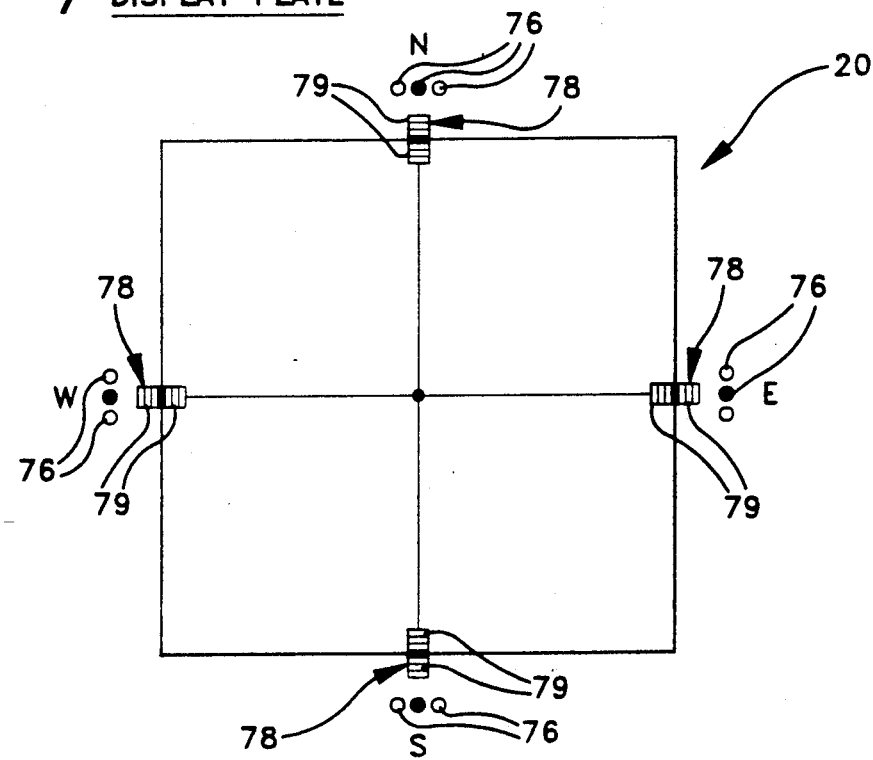

FIG-9

| DETECTORS ILLUMINATED | | | LED'S LIT | | |
|---|---|---|---|---|---|
| $D_L$ | $D_M$ | $D_Q$ | $L_{RD}$ | $M_{GR}$ | $R_{RD}$ |
| 0 | 0 | 0 | OFF | OFF | OFF |
| 1 | 0 | 0 | ON | OFF | OFF |
| 0 | 1 | 0 | OFF | ON | OFF |
| 0 | 0 | 1 | OFF | OFF | ON |
| 1 | 0 | 1 | ON | OFF | ON |

FIG-11

| DETECTORS ILLUMINATED | | | LED'S LIT | | | |
|---|---|---|---|---|---|---|
| $D_L$ | $D_M$ | $D_Q$ | $L_{RD}$ | $M_{GR}$ | $R_{RD}$ | |
| 1 | 1 | 1 | 0 | 1 | 0 | ← SHADOW NOT OVER MIDDLE SLIT |
| 1 | 0 | 1 | 0 | 0 | 0 | ← SHADOW OVER MIDLLE SLIT |

FIG-12A
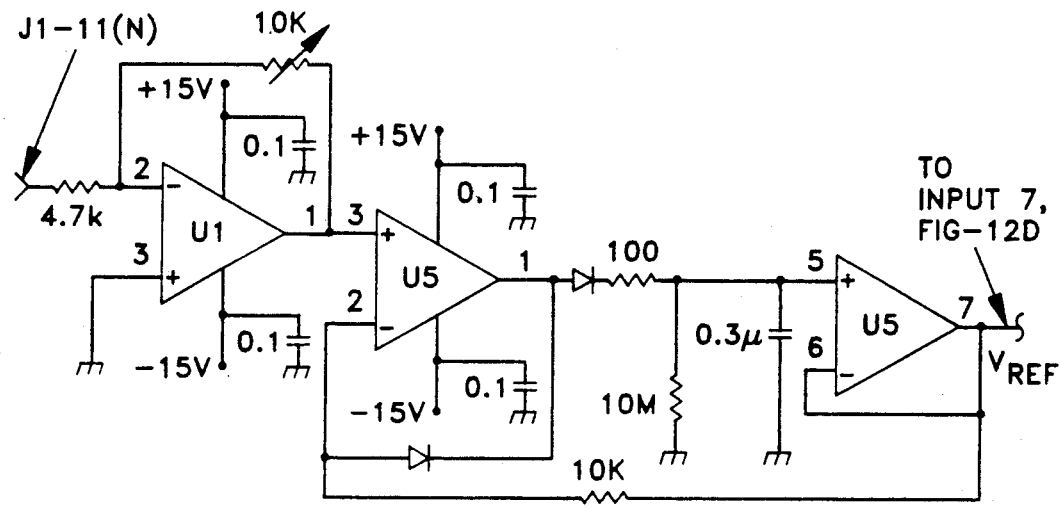
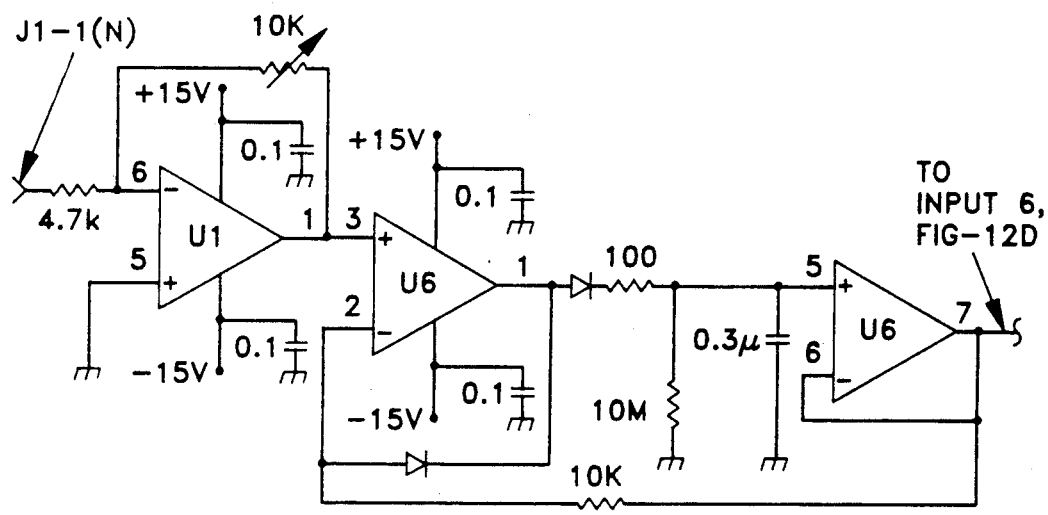
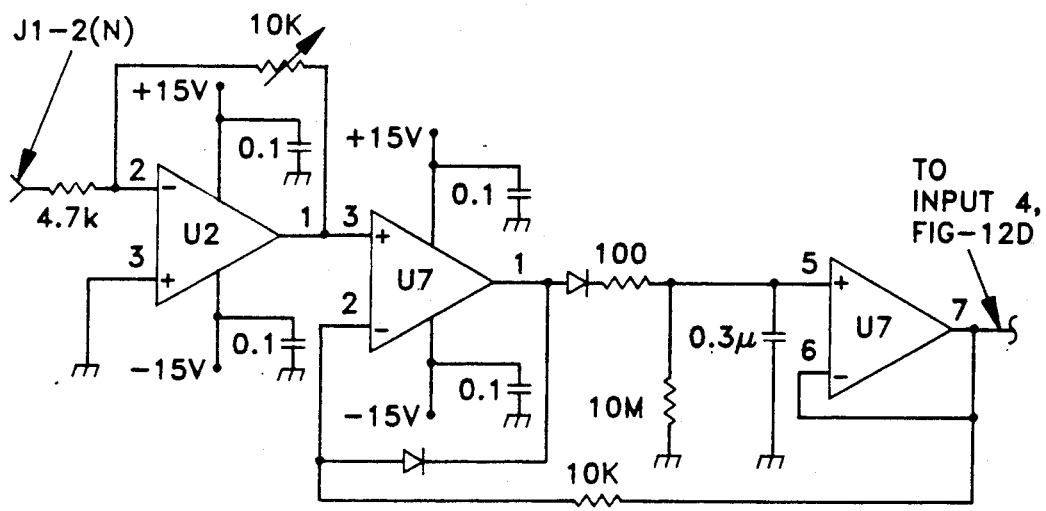

FIG-12B
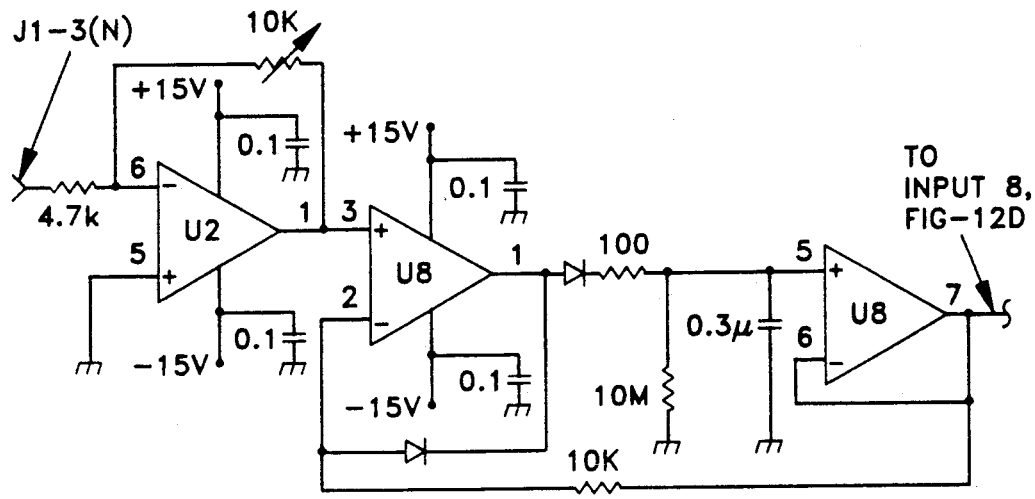
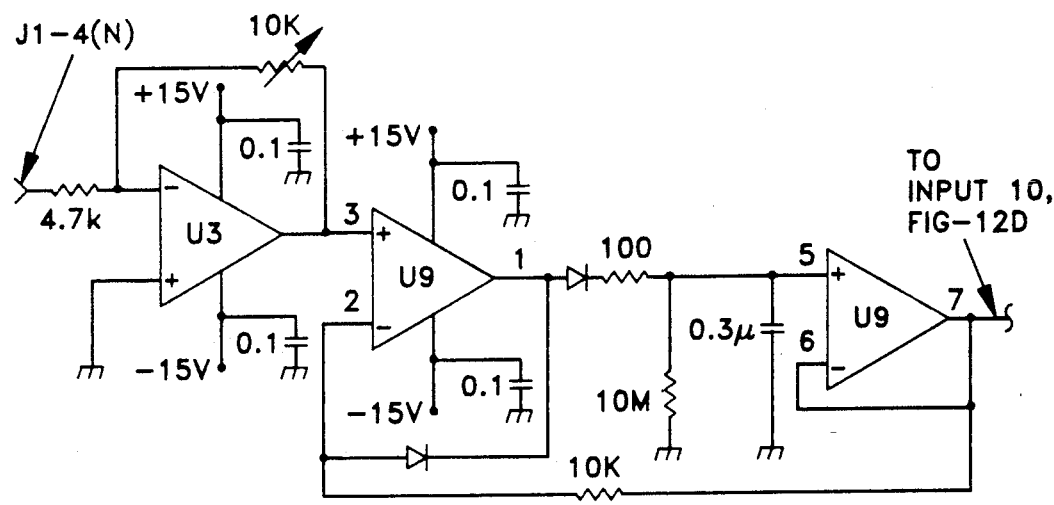
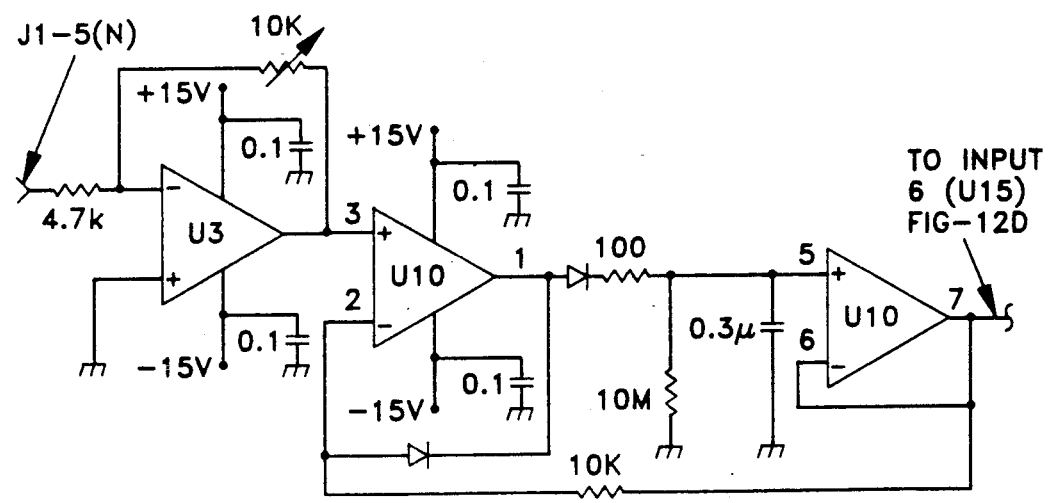

FIG-12C
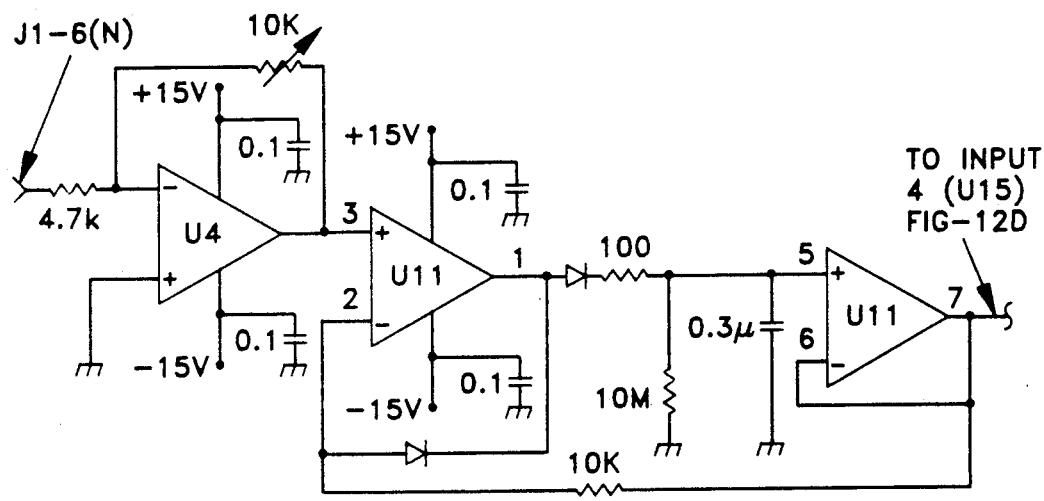
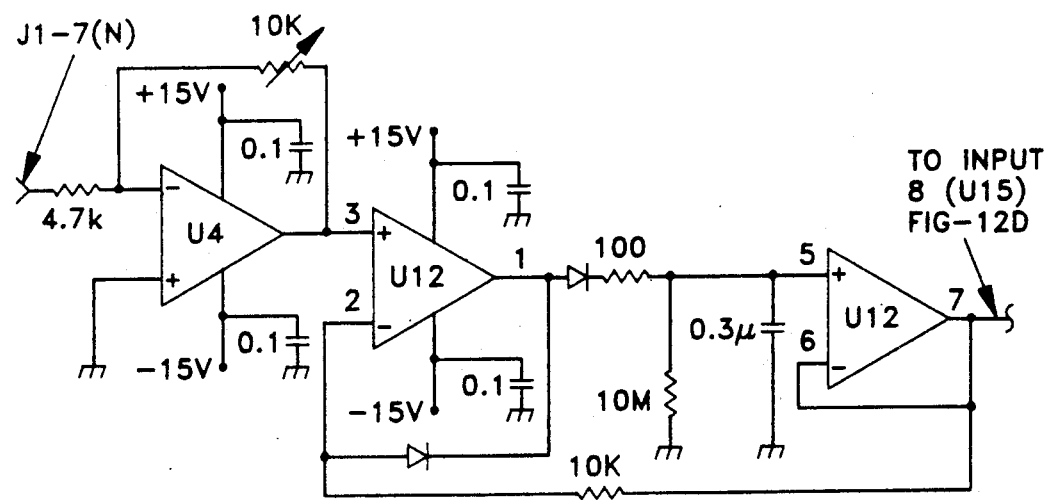

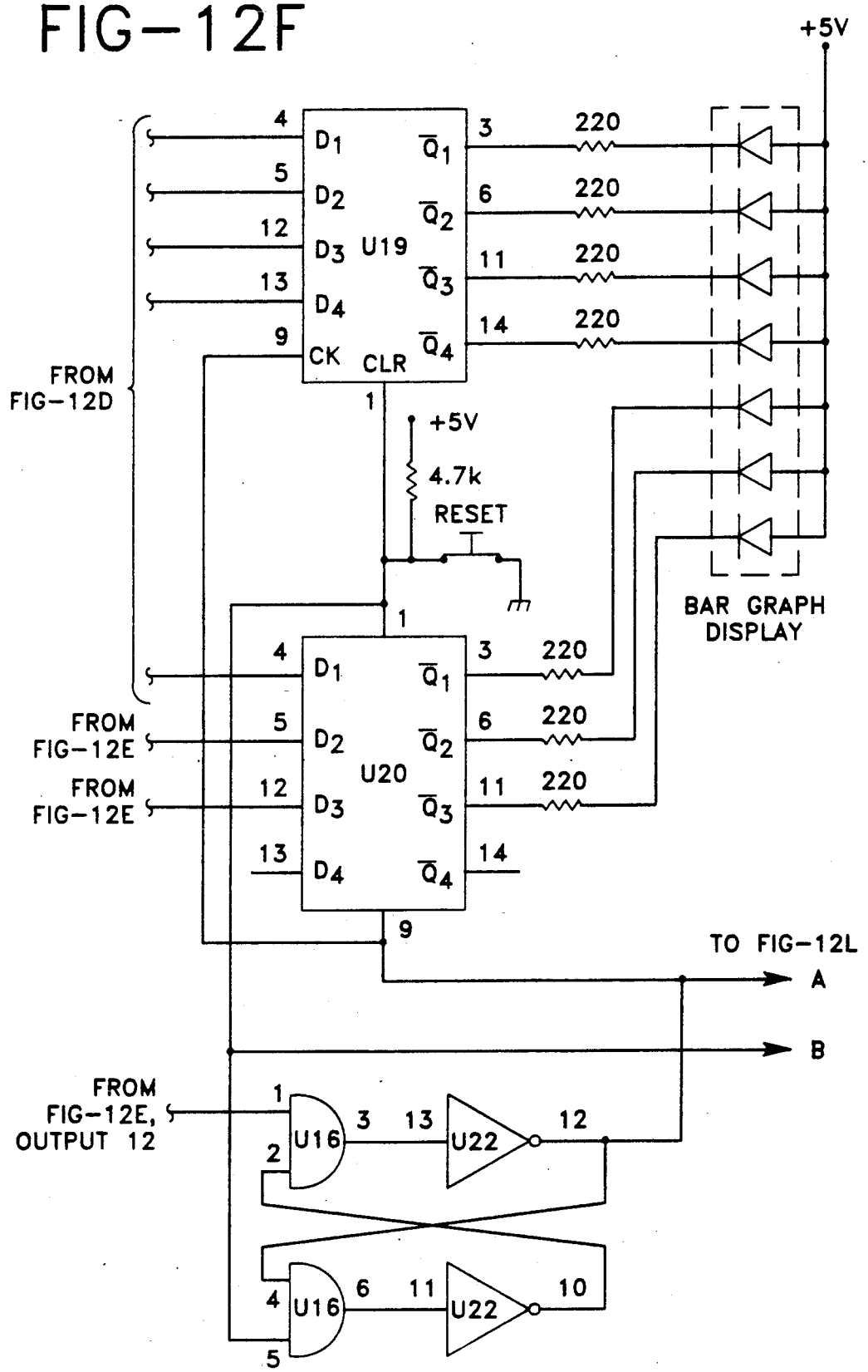

FIG-12H
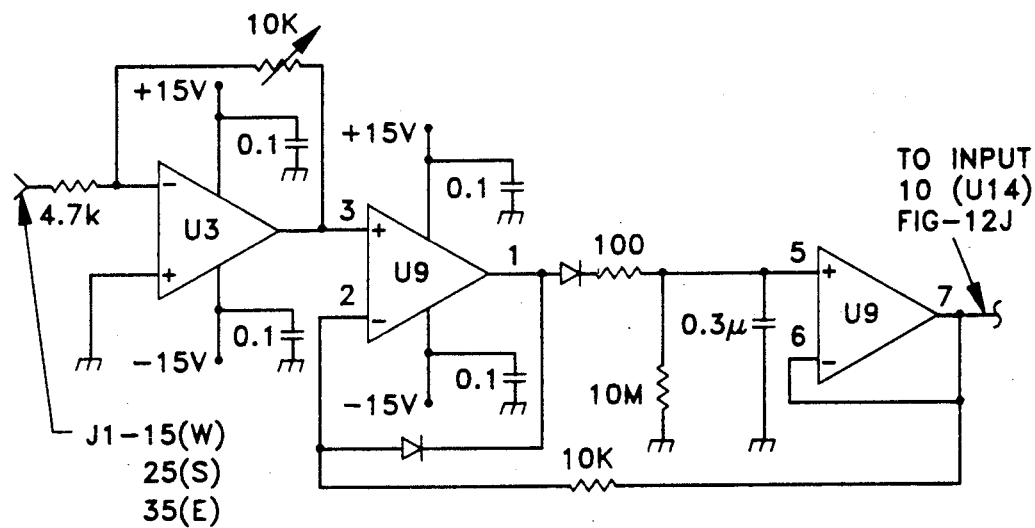
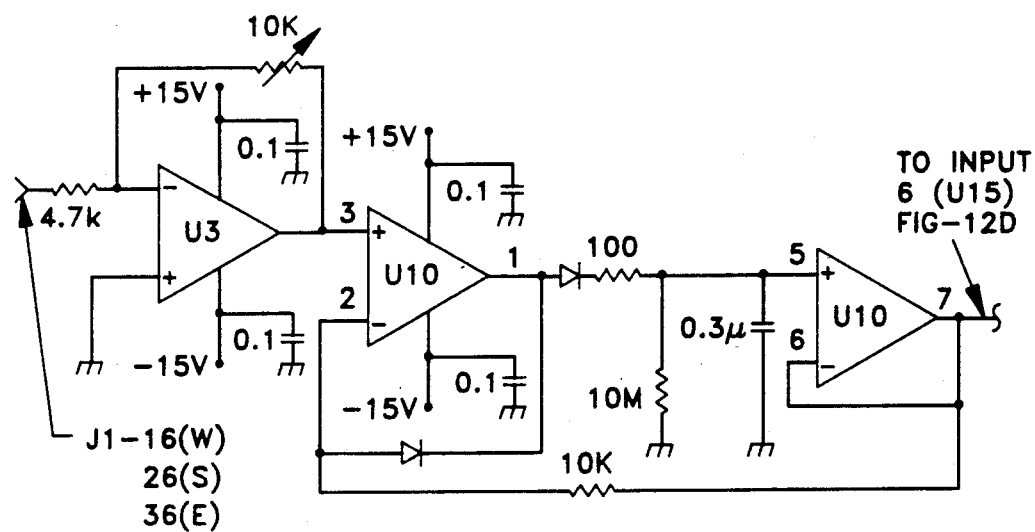

FIG-12I
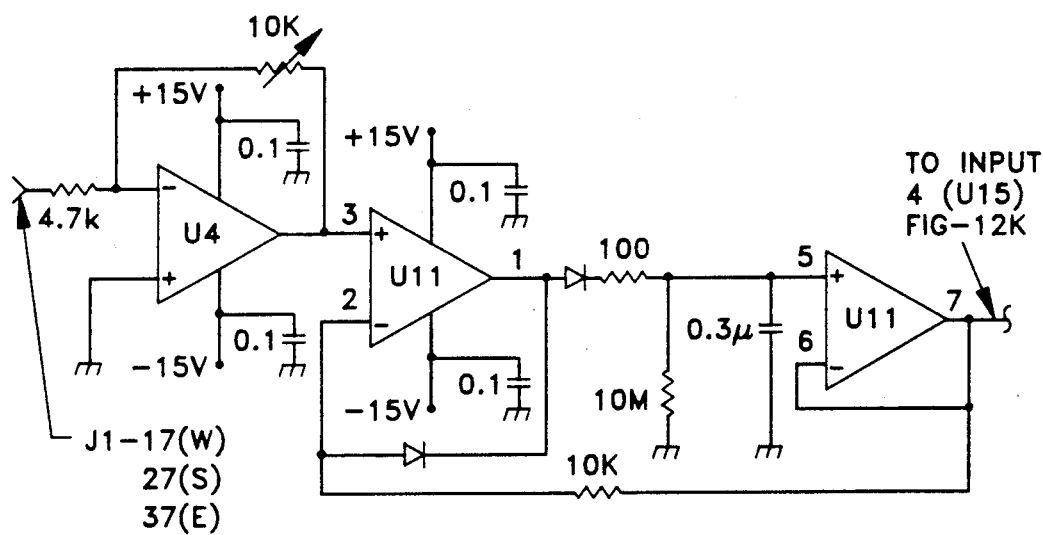
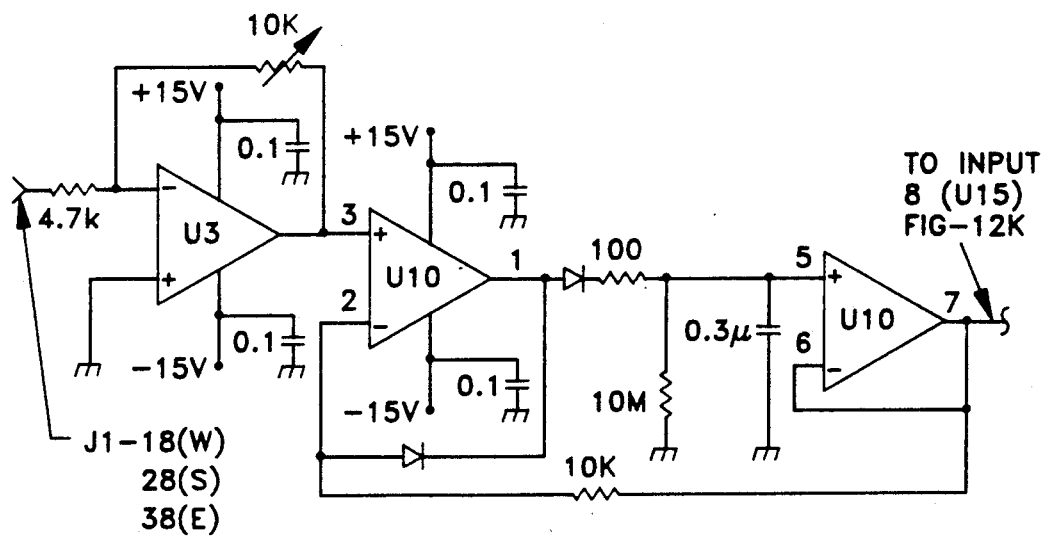

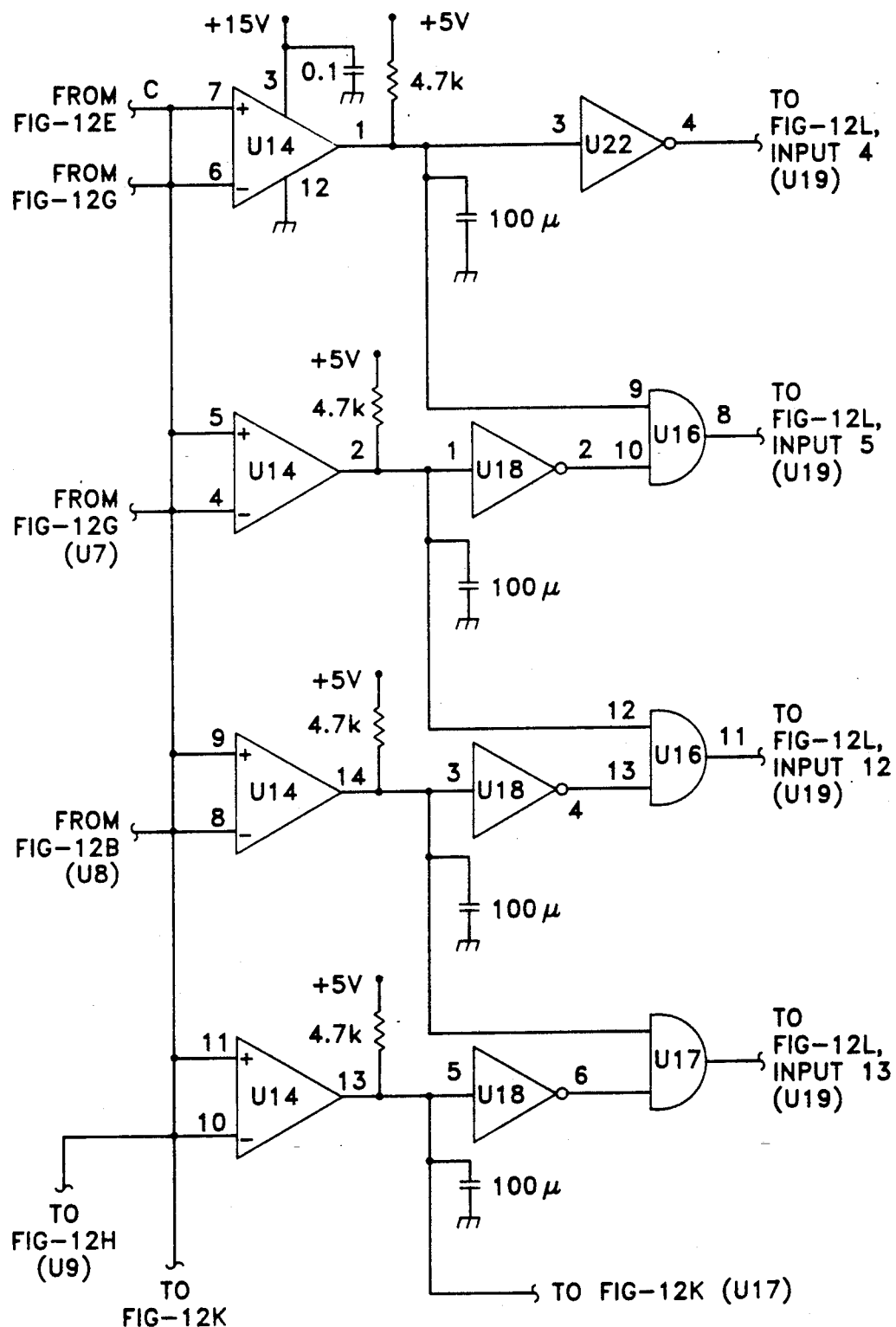

| DETECTOR ILLUMINATION | LED'S LIT |
|---|---|
| NONE | NONE |
| 1 | 1 |
| 1, 2 | 2 |
| 1, 2, 3 | 3 |
| 1, 2, 3, 4 | 4 |
| 1, 2, 3, 4, 5 | 5 |
| 1, 2, 3, 4, 5, 6 | 6 |
| 1, 2, 3, 4, 5, 6, 7 | 7 |

RADIATION DETECTION SYSTEM INCLUDING RADIATION ALIGNMENT MEANS AND ISOCENTRICALLY ROTATABLE DETECTORS

BACKGROUND OF THE INVENTION

1. Field of the Invention

The field of the invention relates to the alignment of radiation instruments such as therapeutic machines and simulators used for cancer treatment.

2. Brief Description of the Prior Art

Various types of radiation equipment require that alignment be checked prior to actual use to insure the radiation will be directed precisely to the target and not elsewhere. Therapeutic machines such as linear accelerators and cobalt treatment machines are two types of such equipment.

Radiation therapy machines used in the radiation oncology departments of hospitals generally include a radiation head mounted to a rotatable gantry. Radiation should be directed by the head to the same point, the isocenter, regardless of the rotational position of the gantry or collimator.

In addition to including means for generating ionizing radiation, the radiation head generally includes an ordinary light source for generating a non-ionizing light beam upon the patient prior to therapy. The head may further include means for generating a target shadow also known as a "cross hair", which becomes visible upon the patient when the light source is actuated. The cross hair is used as one step in insuring that the radiation, such as x-rays, gamma rays or electrons, is directed to a properly positioned patient.

Since the physician or technician must assume that the ordinary light beam is directed at the same point as the subsequently applied therapeutic radiation, it is important that this, in fact, be the case. The conventional method of establishing light/radiation coincidence is to use x-ray film. The film, in its envelope, is first punctured with a needle on the borderline of the light field. It is then subsequently exposed to the radiation. The degree of overlap between the hole marks on the film and the radiation edge indicate the coincidence between these two fields. This technique has several significant drawbacks, namely the subjective marking of the light field and the length of time necessary to process the film. Scanning equipment is also available for scanning the light and radiation fields and determining the coincidence between the two fields and their widths.

A plurality of lasers are also conventionally used to properly position a patient. The lasers are oriented such that each of the beams eminating therefrom intersects each other at the machine isocenter. The beams impinge upon markings upon a patient to insure the patient is positioned to receive radiation from the radiation head only in a specific area. U.S. Pat. Nos. 4,123,660 and 4,223,227 disclose instruments for aligning lasers which include mirrors for detecting any divergences from the main beams.

SUMMARY OF THE INVENTION

It is an object of the invention to provide an instrument which is capable of detecting whether the alignment of a beam of radiation is correct in various rotational positions of a gantry and a collimator.

It is another object of the invention to provide an instrument capable of detecting whether two beams are coincident or not.

A still further object of the invention is to provide an instrument capable of checking the optical distance indicator of a radiotherapy machine.

A still further object of the invention is to provide an instrument which is capable of determining whether the alignment of a plurality of laser beams is correct.

A still further object of the invention is to provide an instrument capable of all of the above functions.

In accordance with these and other objects of the invention, an instrument is provided which includes a mounting fixture, a detector assembly mounted to the mounting fixture, the detector assembly including radiation detection means, first means for rotating the detector assembly about a first axis with respect to the mounting fixture, second means for rotating the detector assembly about a second axis with respect to the mounting fixture, the first and second rotating means maintaining the isocentricity of the detector assembly in substantially all rotational positions. The first and second axes are perpendicular to each other. A camera or the like may be aimed at the isocenter to provide an enlarged image of the detector assembly, which may be displayed on a monitor.

A detector assembly in accordance with the invention preferably includes a substantially planar top surface. The detection means include a plurality of radiation detectors, such as photodiodes, or a phosphorescent screen. The radiation detectors are preferably arranged in a staggered configuration a selected distance from the isocenter. This allows the radiation levels near the "edge" of a radiation or light field to be detected. The relative positions of two different fields can be compared by noting whether the radiation levels of each drop off at the same points. Coincident beams should result in radiation levels which drop off in substantially the same positions near the "edges" of the respective fields.

The detector assembly in accordance with the invention also preferably includes a top surface upon which a target shadow or cross hair can be observed. The isocenter may be marked by a plurality of concentric circles of ellipses. Ellipses are preferred as they appear as circles when the top surface of the assembly is viewed at an angle.

The detector assembly may also include a second set or sets of staggered radiation detectors. At least two such sets are provided, the two sets forming substantially a right angle with the isocenter. If the cross hair passes through certain of the detectors in each set, it is properly aligned. The alignment of other light sources, such as lasers, can also be determined by noting which detectors in the sets are actuated.

If a phosphorescent screen or the like is employed as the detector assembly, it is provided with a border, a pair of intersecting lines, and one or more circles or ellipses marked upon the surface thereof. The border is preferably trapezoidal and corresponds with the edges of the light field generated by the radiation equipment on the detector plane. The pair of lines intersect at the isocenter, and the centers of the circles or ellipses are at the isocenter. Such markings may be provided on non-phosphorescent detector assemblies as well. Since the operator is provided with an enlarged view of the surface of the detector assembly, he can easily observe any misalignment of the radiation equipment or associated lasers and make the proper adjustments.

Methods of determining light/radiation field coincidence, laser alignment, and cross hair alignment are also provided by the invention. Each of the methods can be performed with an apparatus as described above.

The light field/radiation field coincidence test may be performed by providing a detector assembly including means for detecting radiation intensity at a plurality of points within a selected area, directing a light beam at the detector assembly such that a light field is defined upon the detector assembly, the light field including an area of relatively high intensity and a border about this area of declining intensity, the detecting means detecting the declining intensity of at least part of the border. The light beam is then discontinued, and a radiation beam directed towards the detector assembly. The radiation beam causes a radiation field to be defined upon the detector assembly, the radiation field including an area of relatively high intensity and a border about the area of declining intensity. The detecting means detects the radiation intensity of at least part of the border. The outputs of the detecting means in response to the light and radiation beams are compared to determine whether the borders of the respective fields are substantially coincident.

The cross hair test is conducted by directing a light beam at the detector assembly, causing a target shadow in the form of a cross hair to be defined upon the detector assembly, and detecting the light radiation intensity upon the detector assembly at a plurality of points thereon adjacent to the cross hair or intersecting the cross hair.

Laser alignment may be conducted by directing a laser beam towards a detector assembly, and detecting whether the beam crosses selected detectors within the detector assembly.

The isocentricity of the gantry and collimator may be determined by observing the position of the cross hair with respect to a marked isocenter of the detector assembly. The gantry and detector assembly may be rotated in the same direction and the same number of degrees to determine whether the center of the cross hair remains within an acceptable distance of the isocenter of the detector assembly. The collimator is tested by rotating it with respect to the detector assembly and observing the center of the cross hair with respect to the isocenter of the detector assembly. By magnifying the user's view of the surface of the detector assembly through the use of a videocamera and monitor or the like, the relative positions of the cross hair and isocenter can easily be observed.

The radiation field size can be checked by activating the radiation apparatus and observing the field generated upon the surface of the detector assembly with respect to a border marked upon this surface. Such observation is preferably conducted outside the room where the radiation equipment is located by viewing the surface of the detector assembly on a monitor or the like which is located outside the room.

Laser alignment may be checked by observing the lines illuminated by the lasers at least one axis marked upon the detector assembly and passing through the isocenter thereof. If the illuminated lines pass through the isocenter and are substantially collinear with the marked axis or axes, they are properly aligned.

The individual tests described above may be selected on the basis of the type of detector assembly employed.

If radiation detectors are incorporated within the detector assembly which transmit signals upon the detection of radiation, one set of tests may be employed. If the detector assembly is of the type including a phosphorescent screen and a border, a pair of intersecting axes, one or more centrally positioned circles marked on the surface of the screen, a different set of tests are employed. The detector assembly in either event is preferably rotatable about a pair of perpendicular axes and isocentric.

BRIEF DESCRIPTION OF THE DRAWINGS

FIGS. 6a-6c are schematic diagrams of preamplifier circuits associated with the edge and laser detectors of the detector assembly;

FIG. 7 is a top schematic plan view of the top surface of the display plate;

FIG. 9 is a truth table indicating which light emitting diodes are illuminated upon illumination of a set of three photodetectors;

FIG. 11 is a table illustrating which light emitting diodes are illuminated during a cross hair test;

FIGS. 12A-12L are circuit diagrams illustrating an edge detection circuit;

DETAILED DESCRIPTION OF THE INVENTION

Figure 1:
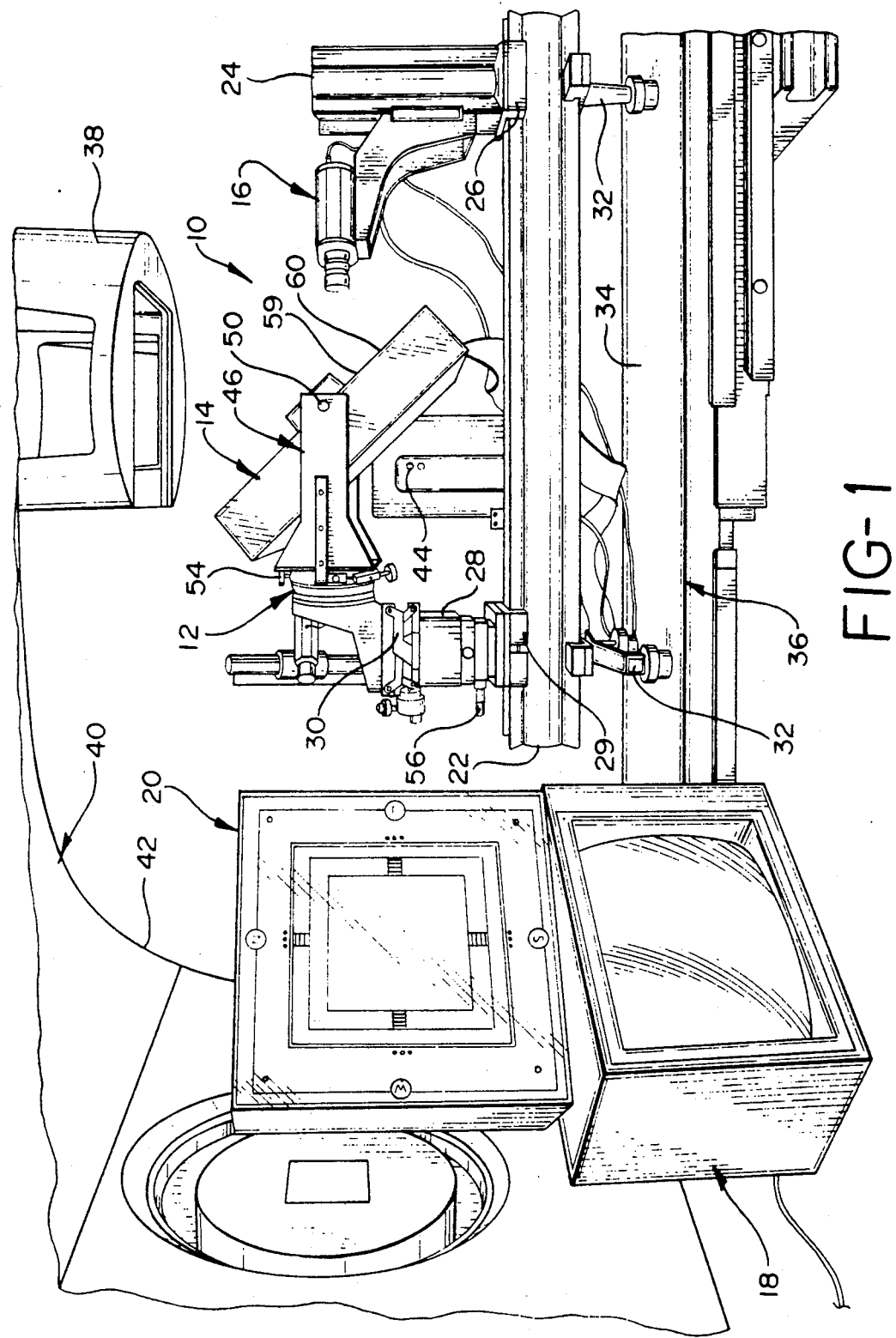
FIG. 1 is a perspective view of a first embodiment of the invention for checking the alignment of a radiation therapy machine.

A system 10 for determining whether a radiation therapy machine or the like and other associated devices are properly aligned is shown in FIG. 1. The system includes the following basic components: a rotary stage 12, a detector assembly 14 pivotably mounted to the rotary stage, a video camera 16, a monitor 18, and a display panel 20. The detector assembly is isocentric, and the camera is aimed at the isocenter thereof.

Figure 2:
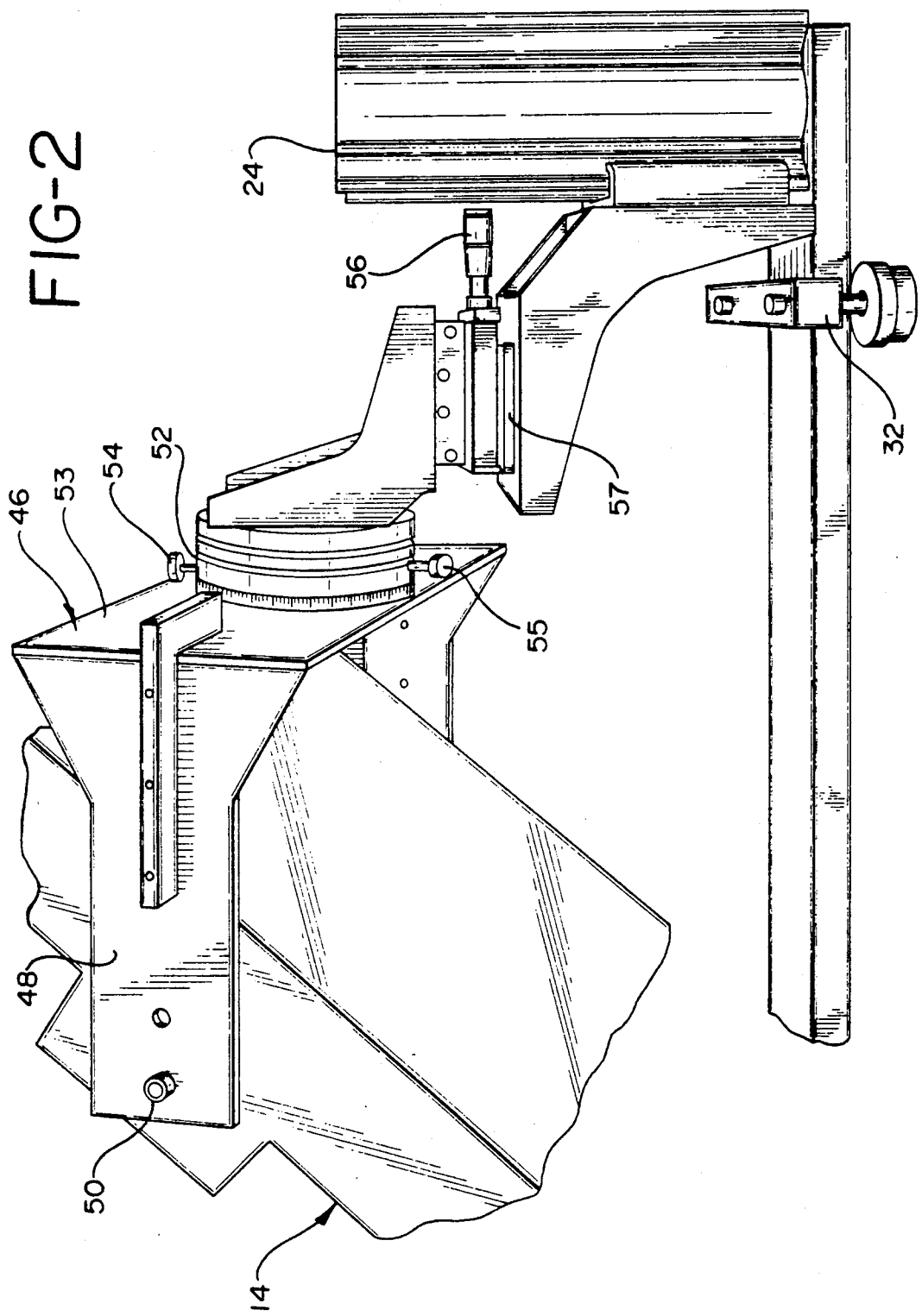
FIG. 2 is a rear perspective view of a detector assembly and support thereof.
Figure 3:
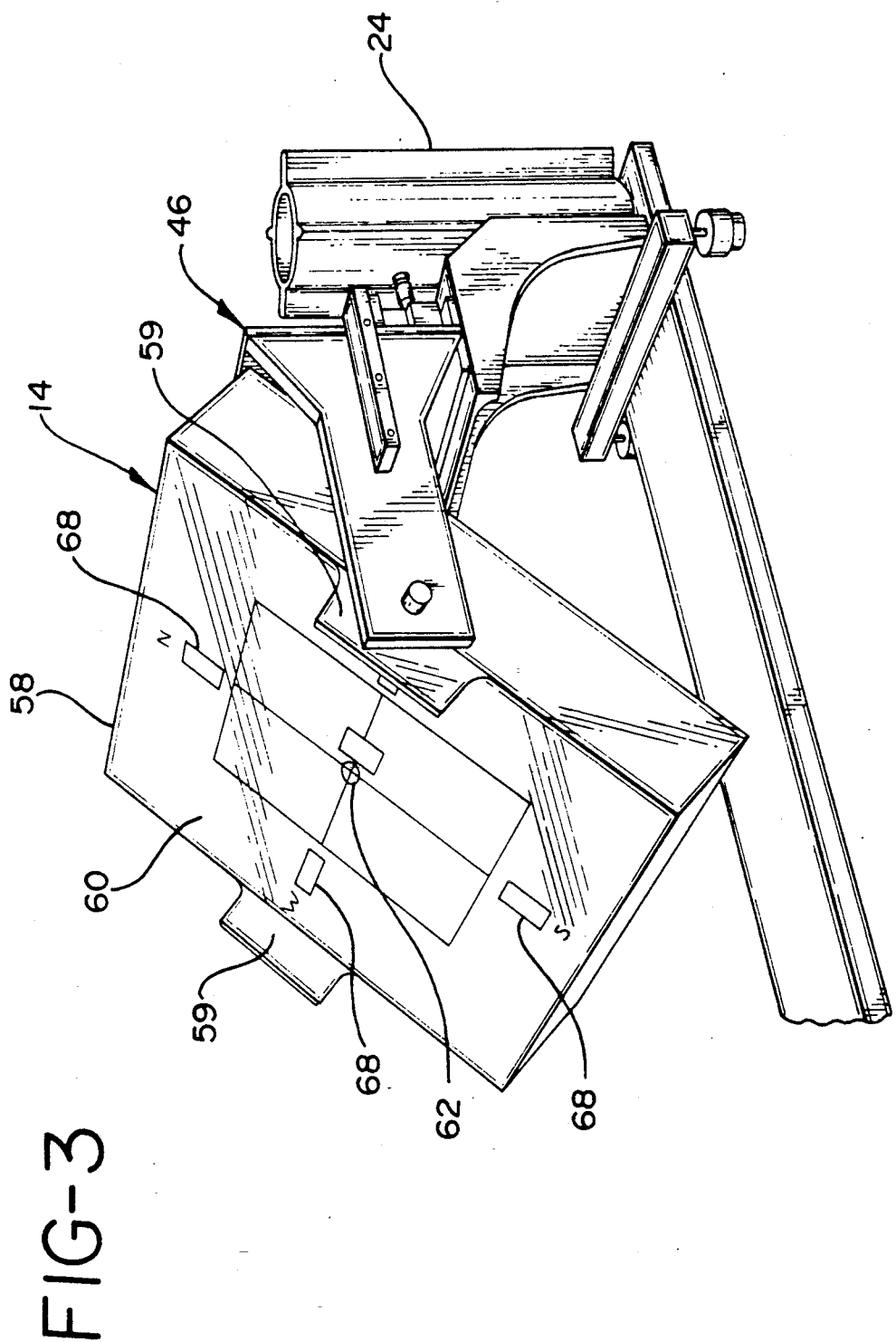
FIG. 3 is a front perspective view thereof.
Figure 4:
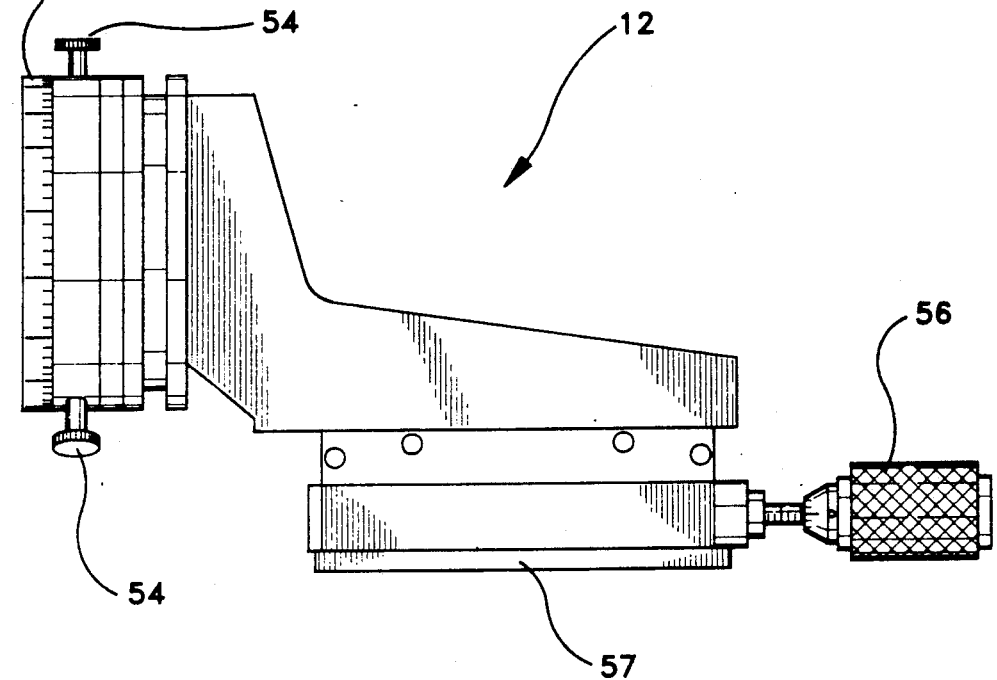
FIG. 4 is a side elevation view of a portion of a rotary stage and associated support bracket.

The rotary stage 12 and camera 16 are both movably mounted to a support rail 22 having a cylindrical base and four projecting flanges. The camera shown in FIG. 1 is secured to a vertical support 24 including a clamp-like base 26 which engages the support rail. (Alternatively, as shown in FIGS. 2-3, the detector assembly 14 may be mounted to this support 24). The rotary stage is mounted to a tower 28 which includes a similar, clamp-like base 29. By loosening the clamp-like bases of the camera support and/or the fixture, the operator may slide either structure along the rail. The rotary stage 12 may be moved vertically by means of a translational stage 30 supported by the tower. Three legs 32 are clamped to the support rail 22. The foot portions of the legs engage the horizontal upper surface 34 of the table 36 which is later used to support a patient.

The detector assembly 14 is positioned directly beneath the collimator 38 of a radiation therapy machine 40 such as a linear accelerator. The collimator 38 is mounted to a rotatable gantry 42 so that radiation may be directed towards a patient from a number of radial directions. The gantry is rotatable about a horizontal axis which runs parallel to the longitudinal axis of the support rail 22, and is referred to hereafter as the y axis. The x axis is perpendicular to the y axis in the horizontal plane, and the z axis is normal to the horizontal plane. The collimator 38 is rotatable about the z axis and emanates the light and radiation fields along this axis. Axes y and z intersect at the isocenter. All of the motions of the accelerator 40 are accordingly isocentric if aligned properly. The table 36 for supporting the patient is also rotatable isocentrically.

A plurality of laser sources 44 are positioned about the table. Each laser directs a beam of light towards either a patient positioned upon the table 36 or the detector assembly 14, whichever is in the light path. In either case, an illuminated line is formed on the target by each laser beam. Each of these lines should cross the isocenter.

Referring to FIGS. 1-3, the detector assembly 14 is supported by a mounting bracket 46 including a pair of parallel arms 48. The detector assembly 14 is positioned between the bracket arms and pivotably secured thereto by a pair of opposing pins 50. It is rotatable about the arms defined by the pins. The detector assembly may be maintained in a selected rotational position by frictional engagement with the bracket arms or by mechanical locking means.

The mounting bracket 46 is supported by the rotary stage 12. The rotary stage includes a calibrated, rotatable ring 52 to which the back plate 53 of the mounting bracket 46 is secured. The calibrated ring 52 and mounting bracket 46 are accordingly rotatable about an axis which is perpendicular to the axis defined by the pivot pins 50. The position of the center of the detector assembly 14 does not change regardless of the rotational position of the bracket 46 with respect to the rotary stage. In other words, the rotary stage 12 and mounting bracket 46 allow the detector assembly to be rotated about two axes while maintaining its isocentricity.

One or more set screws 54,55 are provided for fine tuning the rotational position of ring 52 locking the ring 52 in any rotational position, respectively. The calibration markings on the ring 52 indicate the rotational position of the detector assembly 14. These markings allow the operator to correlate the rotation of the gantry with the rotation of the detector assembly. A third adjustment screw 56 allows the rotary stage 12 to be moved with respect to a mounting plate 57 and parallel to the y axis.

Figure 5:
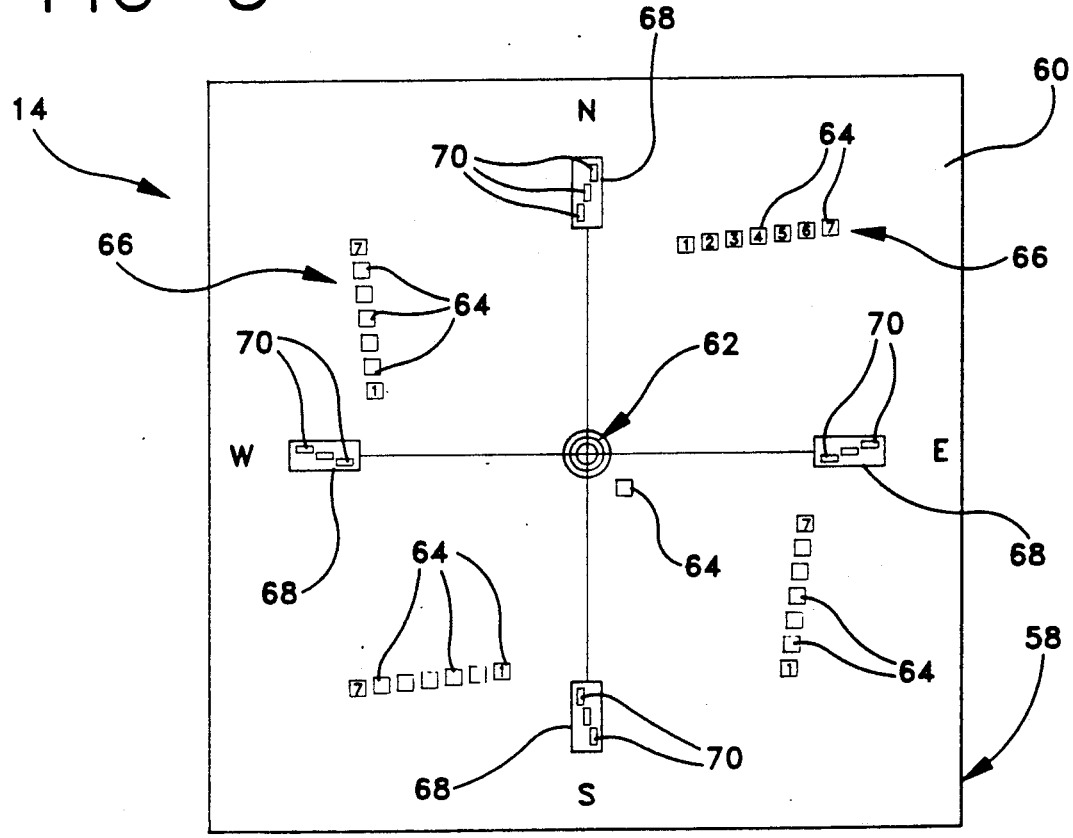
FIG. 5 is a top schematic plan view of the top surface of the detector assembly.

Referring to FIGS. 3 and 5, the detector assembly 14 includes a plexiglass or other substantially transparent housing 58 including a pair of opposing extensions 59 through which the pivot pins 50 extend. The housing includes a substantially square upper wall defining a flat upper surface 60. The isocenter is defined by the centers of three concentric ellipses 62 marked upon this upper surface. A silicon PIN diode 64 having an active area of $2.71 \times 2.71$ mm$^2$ is mounted to the housing beneath the isocenter. It is employed as a reference photodiode.

Four sets 66 of seven similar photodiodes 64, used as "edge" detectors, are arranged at selected radial distances from the isocenter. The photodiodes may be individually mounted to the housing, or parts of an array mounted thereto. Their positions correspond generally with the field sizes of the light and radiation beams which are subsequently directed thereon. In the illustrative embodiment of the invention shown and described herein, the photodiodes 64 in each set 66 are arranged in staggered relationship, the center to center spacings of the stagger being about 0.5 mm. While seven photodiodes are shown in each set, it will be appreciated that a greater or lesser number can be employed. Each of the photodiodes is positioned beneath the transparent upper wall of the housing. It is accordingly important that the upper surface 60 is both clean and substantially free of dust when the detector assembly is employed.

Four opaque, rectangular plates 68 are secured to the upper wall of the housing 58. Each plate includes three slits 70 extending therethrough. The slits are arranged in staggered relationship. The opposing center slits of two opposing plates are positioned on a line 72 provided on the upper surface 60 of the detector assembly 14 and running parallel to or collinear with the axis defined by the pivot pins 50. The other opposing pair of center slits 70 are arranged along a line 74 running perpendicular to the first-mentioned line 72. A photodiode, also referred to herein as a "laser detector", is positioned beneath each of the slits 70.

As shown in FIGS. 6a and 6b, each photodiode 64 (designated as D1-D7 in the figure for the edge detectors, D-right, D-left, and D-middle for the laser detectors) is connected to a transimpedance, FET input, low noise preamplifier, the output of which goes to a fifty pin edge connector designated as J1. The transimpedance preamplifier converts current generated in each diode, due to incident light or radiation, to voltage output. The transfer function of the amplifier is:

$$H(s) = \frac{R_F}{1 + sR_F(C_F + C_i/A)}$$

where:
s = jω
$R_F$ = Feedback resistor
$C_F$ = Feedback capacitor
$C_i$ = Input capacitance of amplifier and detector (Typ. value, 1 pf).
A = Open loop gain ($\approx 300$ at 10 KHz)
The band width (BW) is:

$$BW = \frac{1}{2\pi R_F(C_F + C_i/A)}$$

Using the values from FIGS. 6a and 6b, $$BW_{edge} = \frac{1}{2\pi 330 \cdot 10^3 \cdot 2 \cdot 10^{-12}} = 241 \text{ KHz}$$

for edge detector $$BW^{laser} = \frac{1}{2\pi 10^7 * 2 * 10^{-12}} = 8 \text{ KHz:}$$

for laser detector

For a single pole amplifier the rise time is approximated:

$$t_r = \frac{0.35}{BW}$$

FOR EDGE: $t_r = 0.35/241*10^3 = 1.5$ μsec
FOR LASER: $t_r = 0.35/8*10^3 = 44$ μsec The circuit is fast to respond to radiation pulses, which are about 10 μsec wide, ($t_r = 1.5$ μsec < 10 μsec) and has good low pass (L.P.) characteristics to reduce noise at the amplifier output. For laser detection there is no need for fast electronics since the laser has a constant DC output. Therefore, a low pass filter with 8 KHz cutoff frequency is used to minimize noise.

FIGS. 6a and 6b shows the detailed circuit for the radiation edge and laser detection preamplifiers along one side of the detector plate (n, or North edge). The same circuit is repeated for the other sides of the detector plate, using different pinouts on the edge connector. There is only one reference diode and preamplifier for the whole detector plate, which is used only in connection with the edge detectors.

The top surface of the display panel 20 is shown schematically in FIG. 7. This panel includes a transparent upper wall to which four sets of three indicator lights 76 such as light emitting diodes are mounted. The middle indicator light is preferably a different color (e.g. green) than the remaining two lights (red) of each set. The positions of the indicator lights on the display panel correspond to the positions of the four sets of slits in the plates 68 mounted to the detector assembly housing.

Four sets 78 of seven light emitting diodes 79 are secured to the display panel. Each light emitting diode corresponds to one of the photodiodes in the four sets 66 mounted to the detector assembly 14. One of the light emitting diodes will be illuminated when it corresponds to the photodiode receiving a selected percentage of the peak radiation level, the peak being measured by the center (reference) photodiode in the detector assembly.

Figure 8:
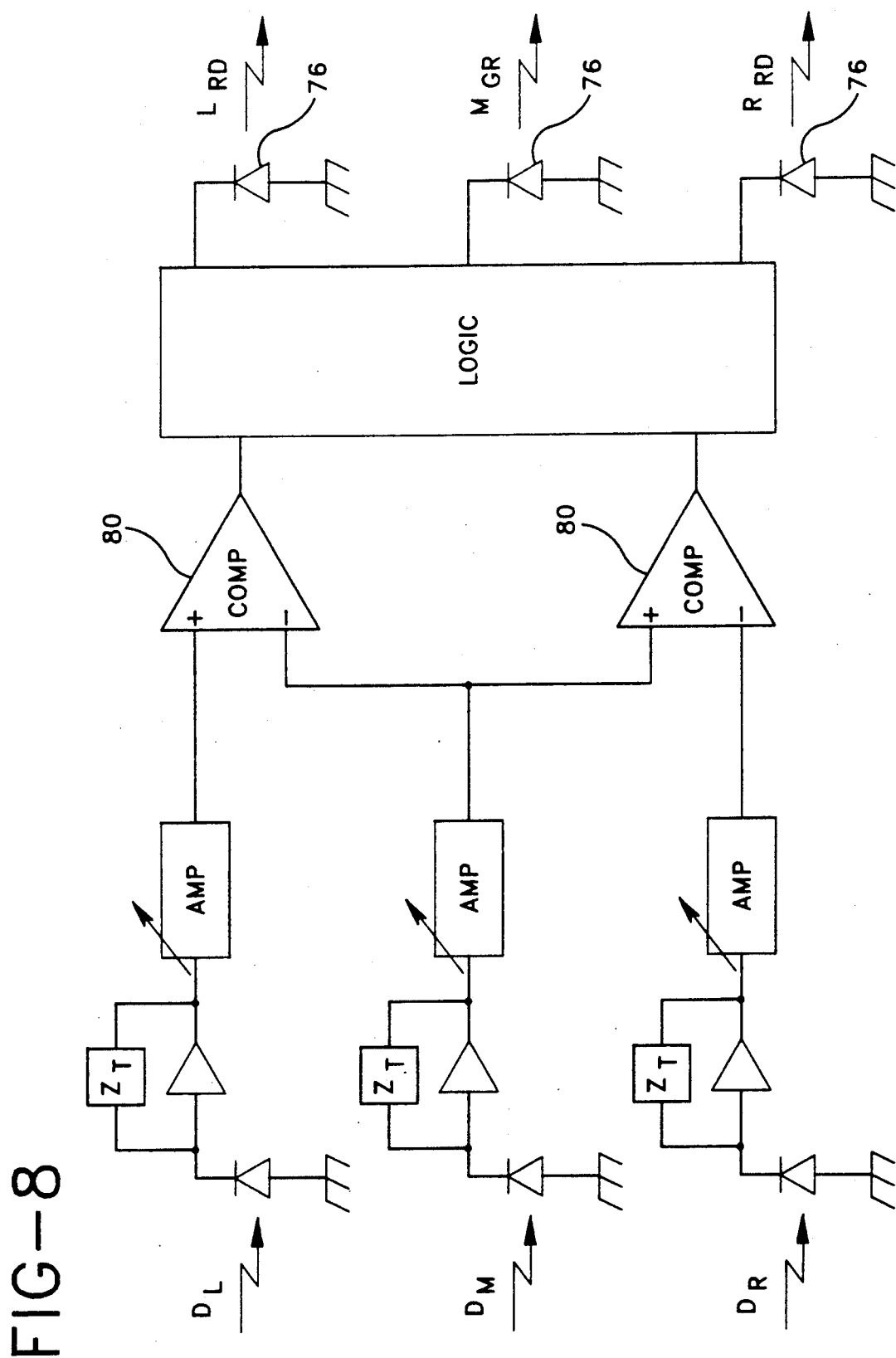
FIG. 8 is a schematic circuit diagram of a laser detection circuit.

The position of each laser source 44 is checked by comparing the intensities (outputs) of the three staggered logic position diodes ($D_L$, $D_M$, $D_R$) shown schematically in FIG. 8. The digital output of the comparators 80 goes to a dedicated logic circuit 82 which in turn lights up the proper LEDs according to the truth table in FIG. 9. When the laser light line passes through the right detector, the right (red) LED lights up, indicating that the laser is misaligned and shifted to the right by the spacing (resolution) between the diodes (0.5 mm). The same is true for the left side. Only when the green LED is lit is the laser properly aligned.

Figure 10A:
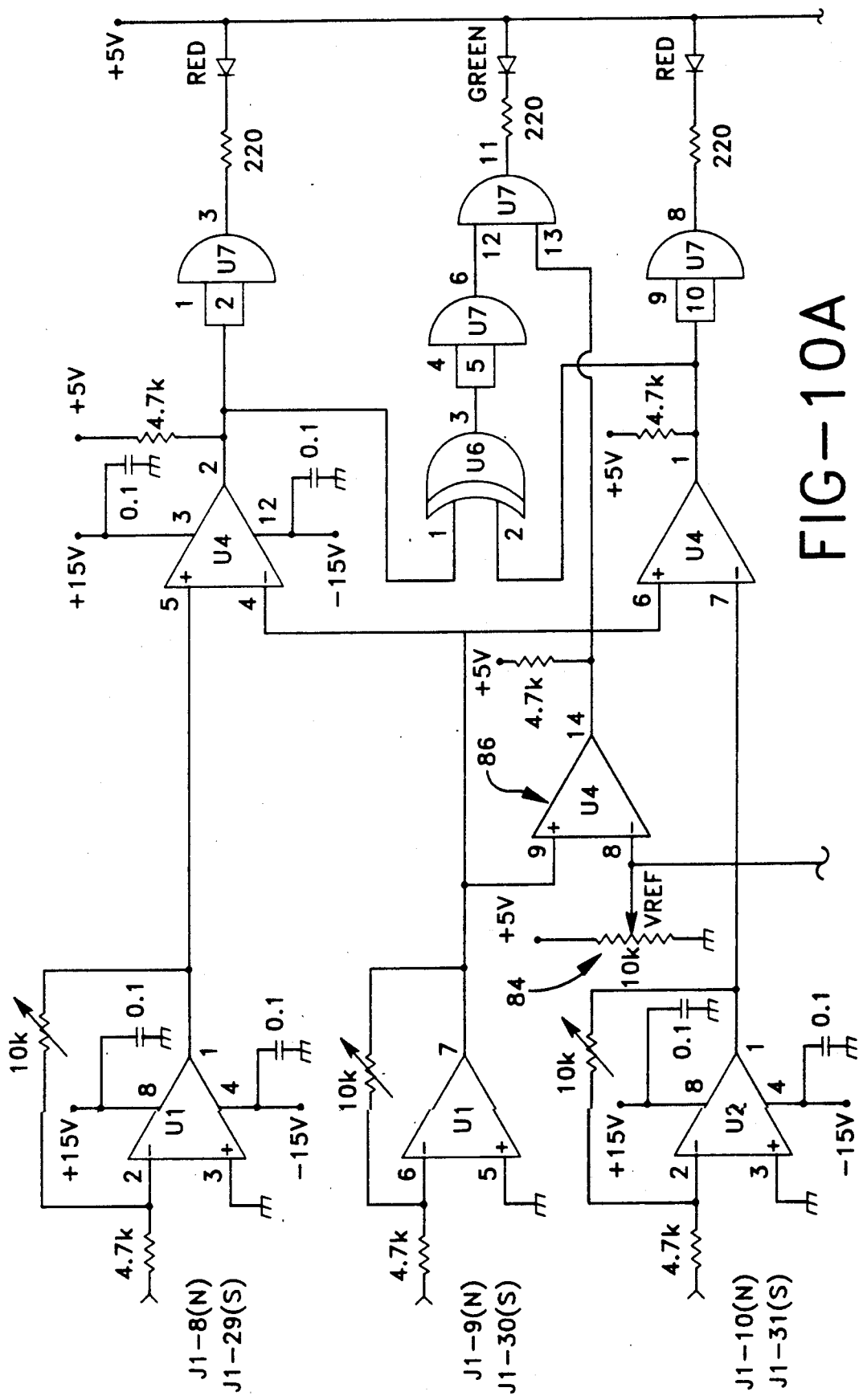
FIGS. 10A-10B are circuit diagrams of a laser detection circuit.
Figure 10B:
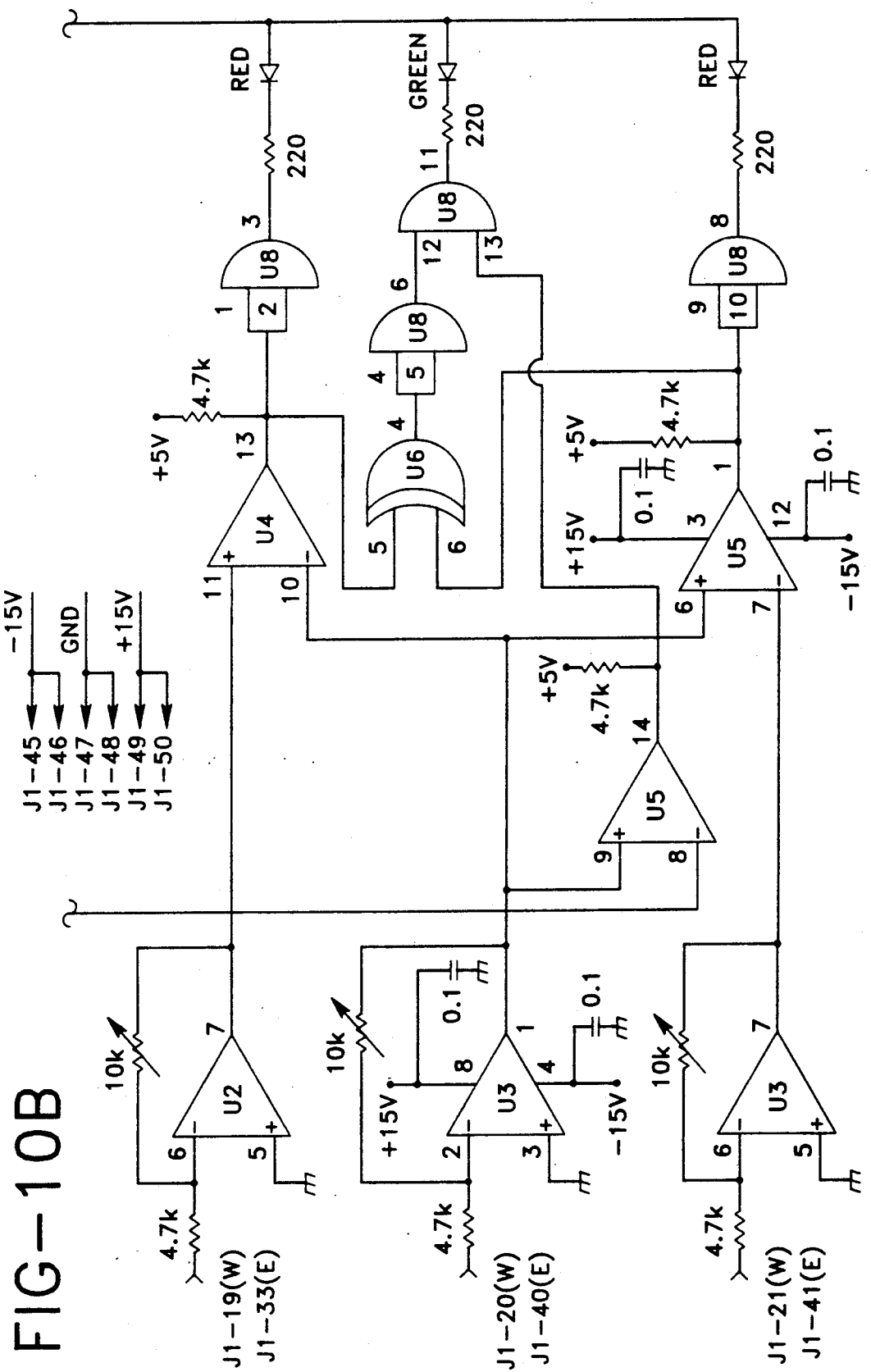
Figure 12D:
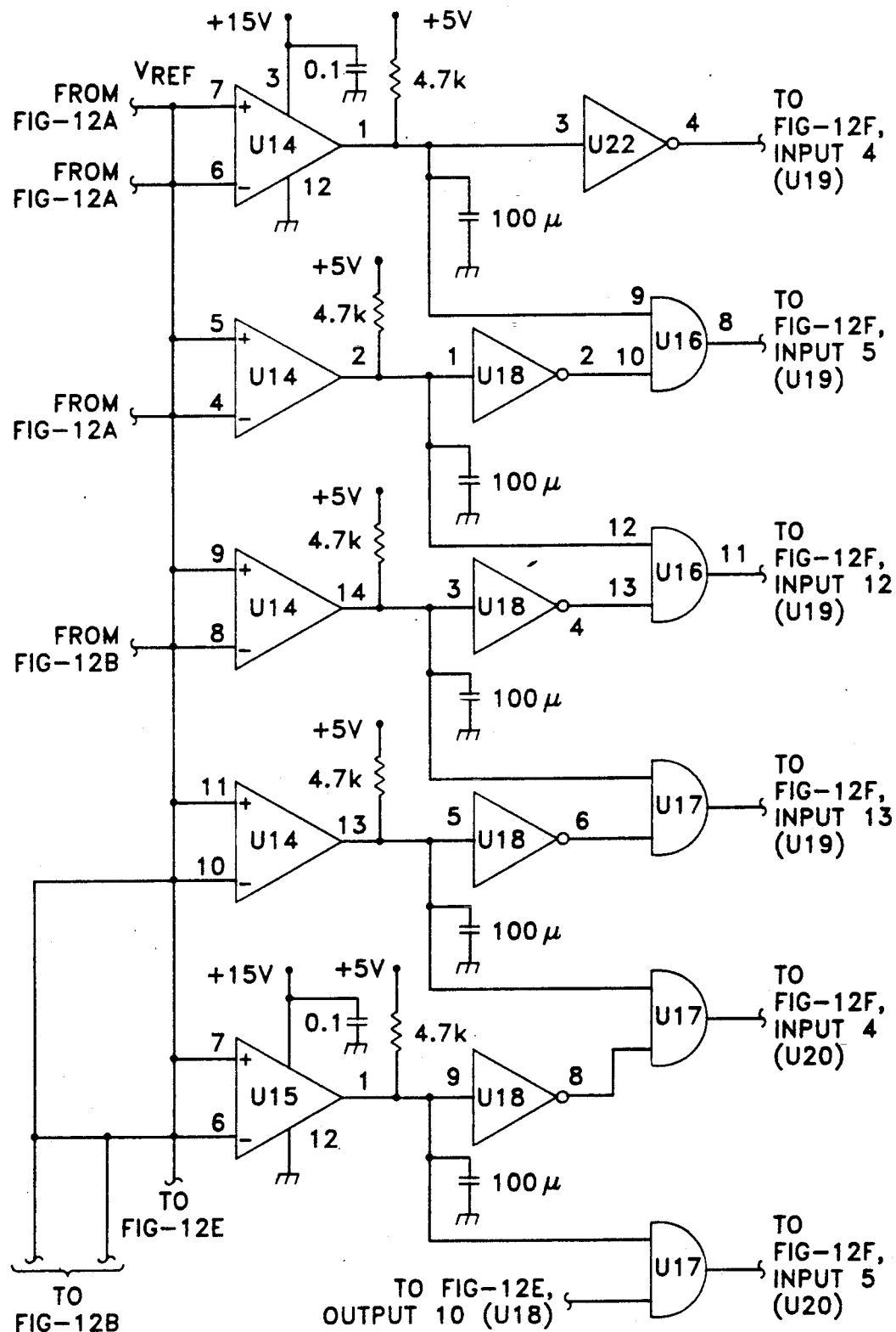
Figure 12E:
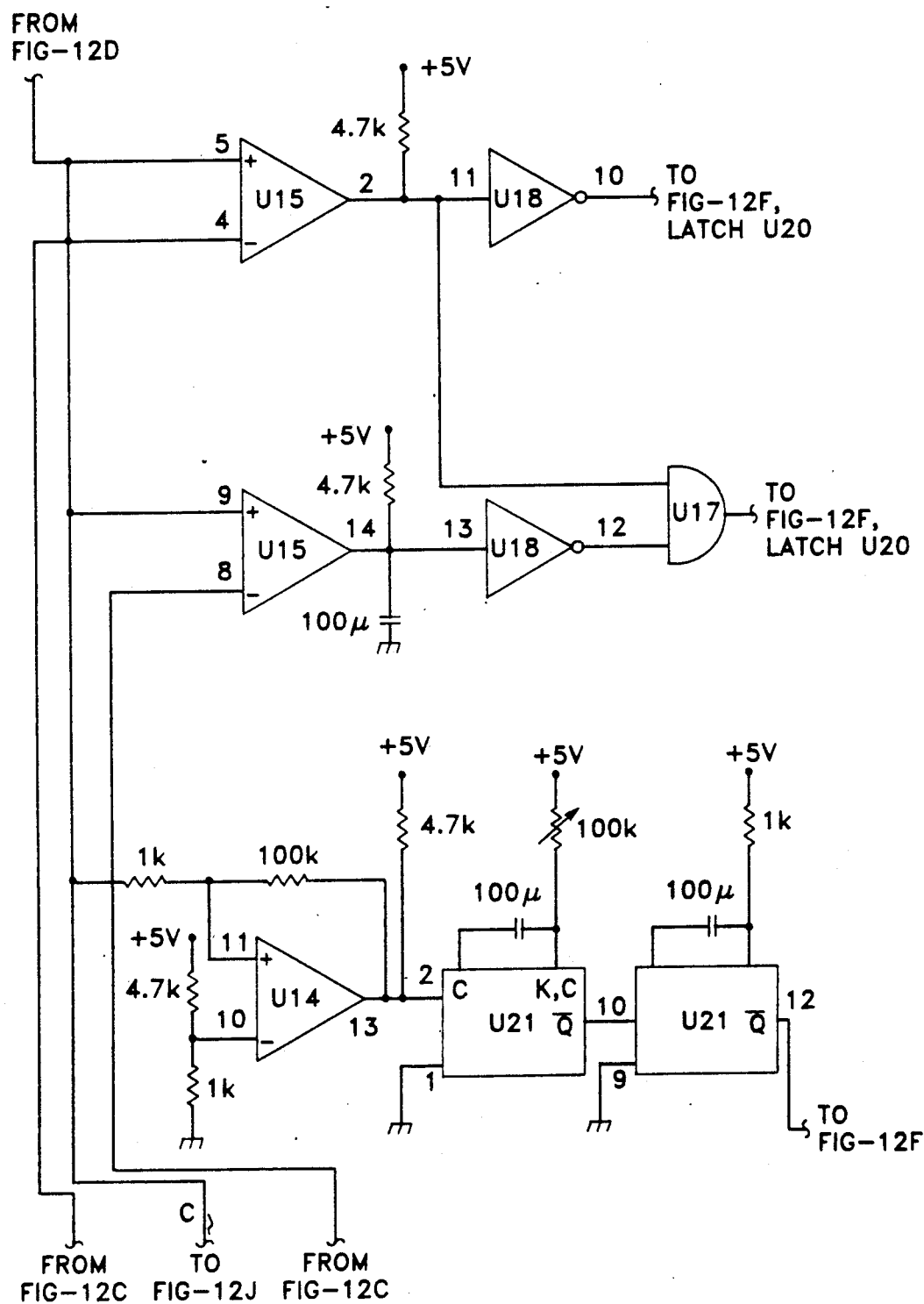
Figure 12G:
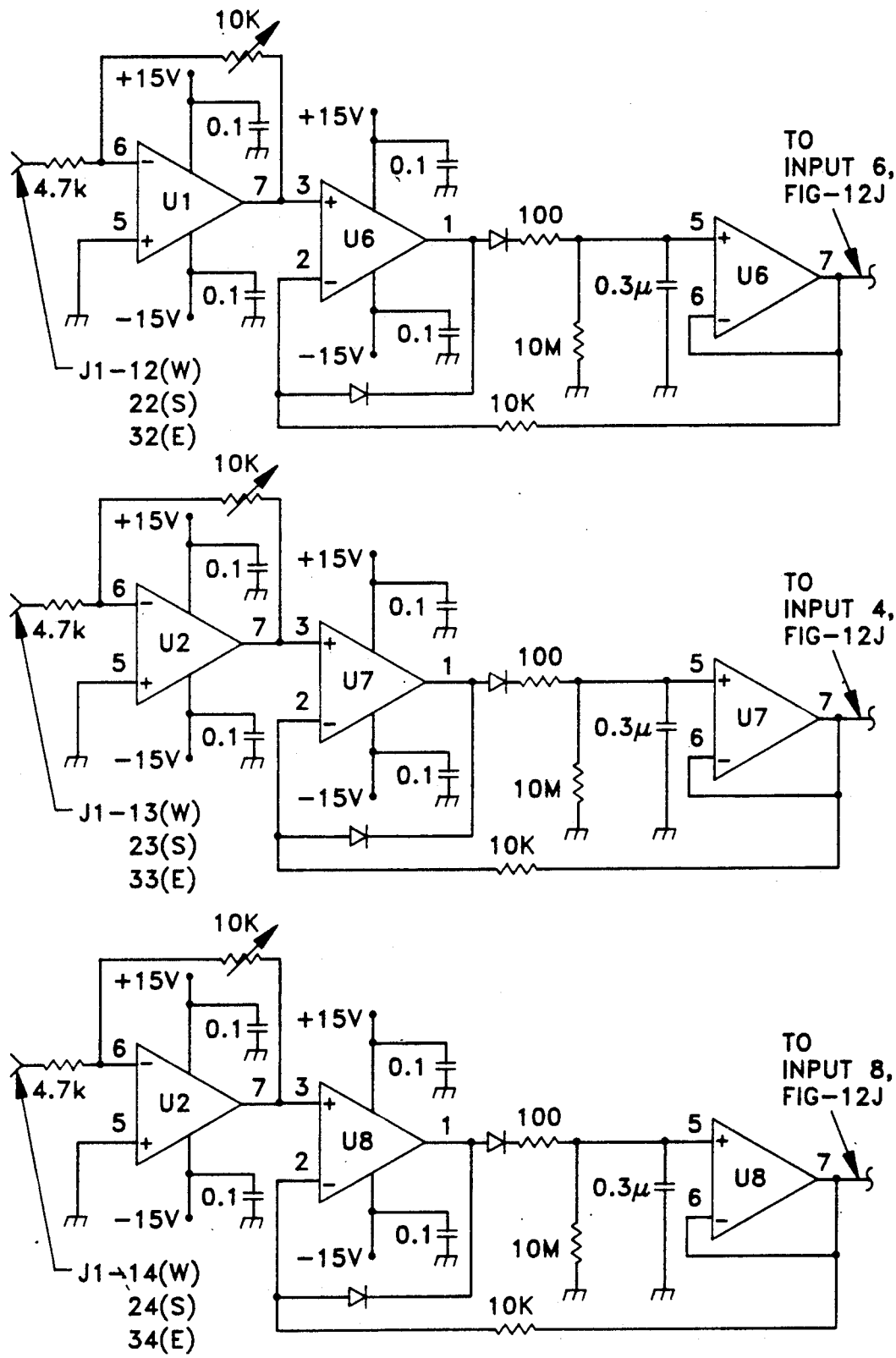
Figure 12K:
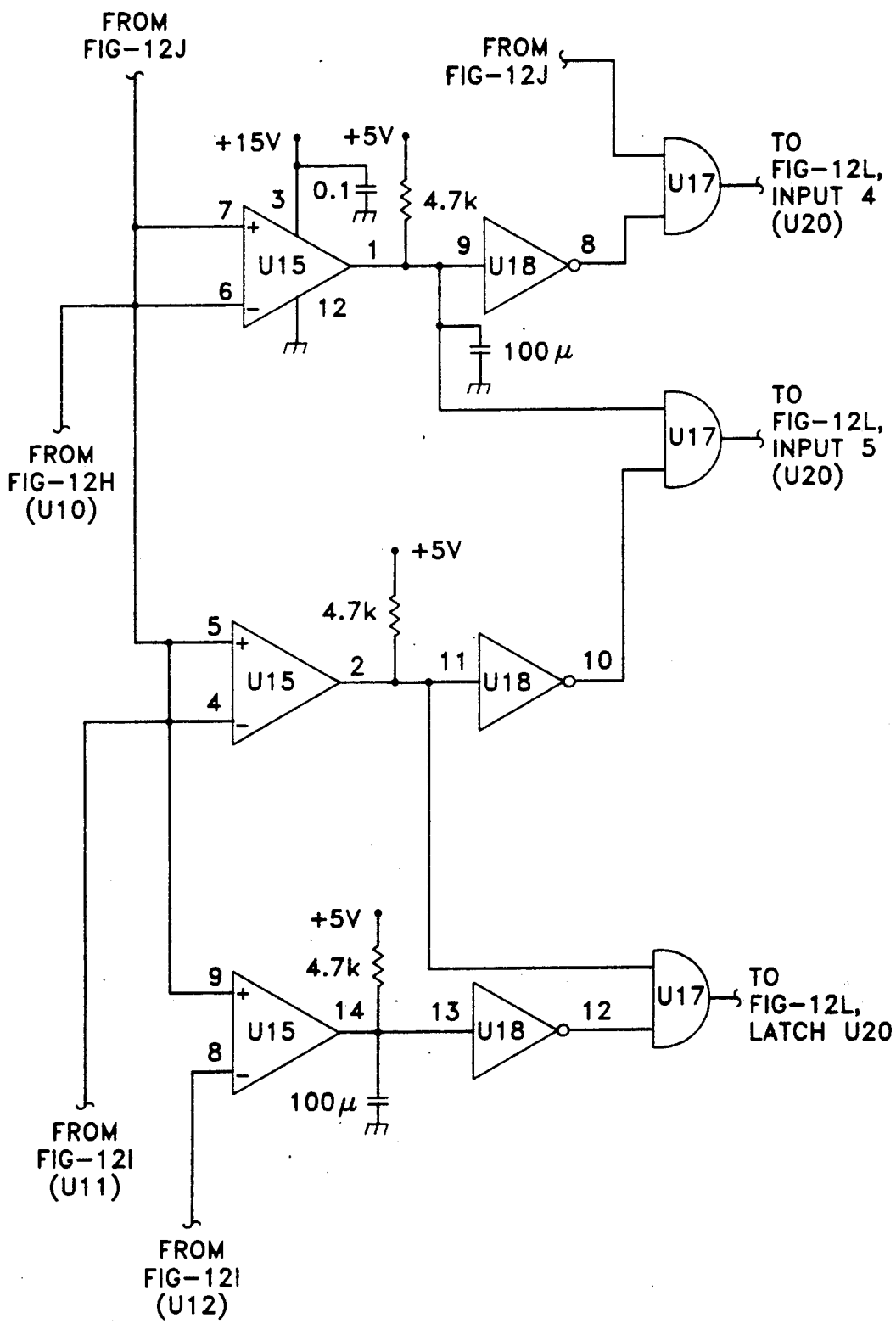
Figure 12L:
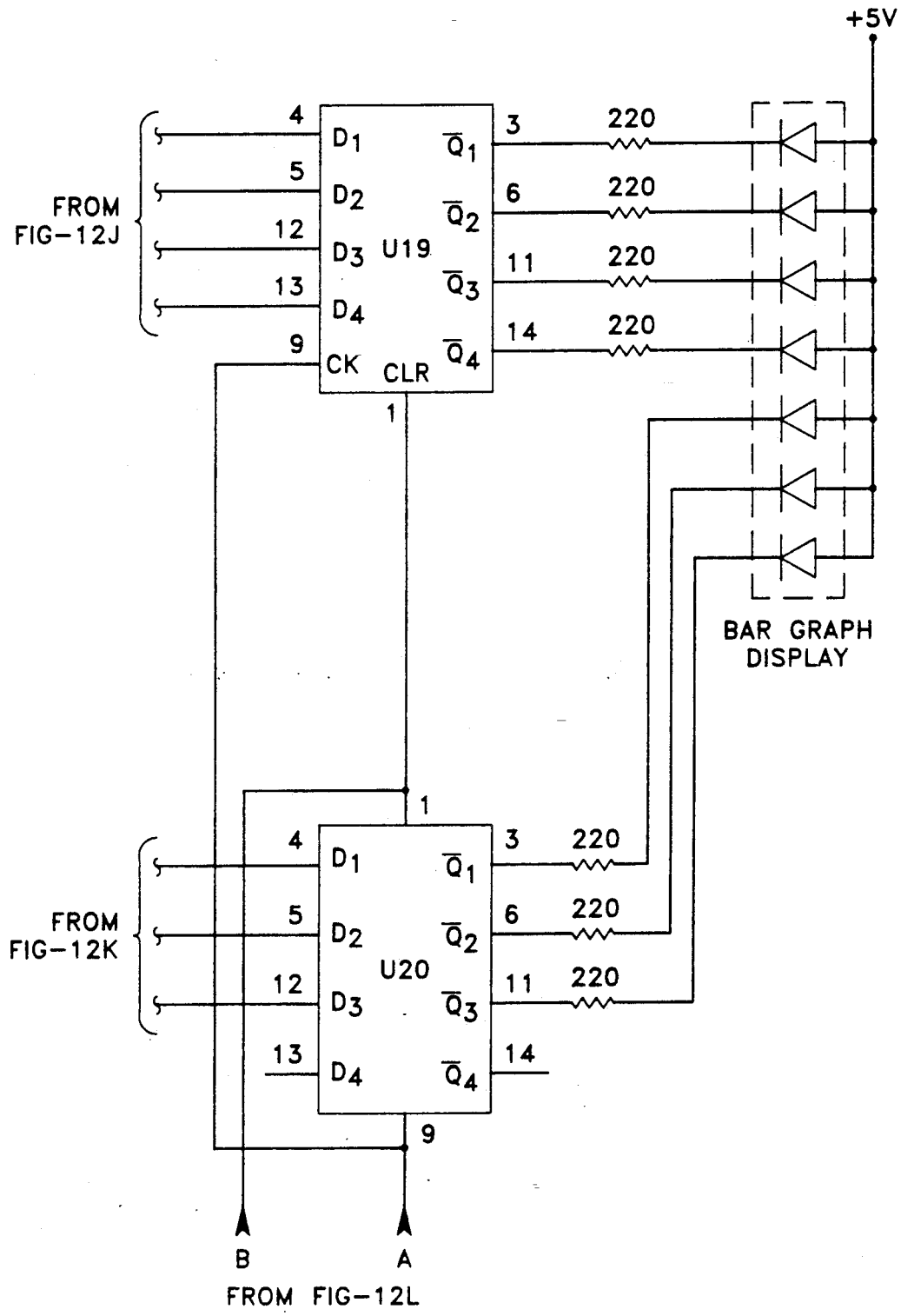

The diode preamplifiers' outputs are connected to the fifty pin connector (J1) and ribbon cable to the display panel 20 which contains the electronic circuit and the display. The left laser detector's ($D_L$) preamplifier is wired to J1-8 (for N) the middle detector to J1-9 and right to J1-10, as shown in FIGS. 10A and 10B. It is symmetric for all sides (S, W, E) and shown on the circuit diagram.

The outputs at the preamplifiers are connected to an adjustable gain amplifier (U1, U2, U3) with a gain of 0 to −2.12.

$$\text{GAIN} = A = -\frac{P}{R}$$

$$A_{min} = \frac{0}{4.7} = 0$$

$$A_{max} = -\frac{10}{4.7} = -2.12$$

From the adjustable amplifier, all three outputs are connected to two comparators, U4, in such a way that the middle detector's output is common to both comparators. In this way the side detectors outputs are compared to the middle one. When the middle detector output is higher that the side detectors, both comparator outputs U4-2 and U4-1 go low ("0"). The red lights turn off (U7-3, and U7-8 in high state "1".) The green light turns on since the exclusive or gate output (U6) is at logical "0". In order to be independent of ambient light and overhead light reflections, the laser alignment test is performed in a darkened room. In such conditions, the amplifiers' outputs are set by the diodes dark currents, and may put the comparators in an ambiguous wrong state. In order for the comparators to be in a controlled and determined state, a reference (Ref.) potentiometer 84 and comparator 86 are employed. Thus, the adjustment of the circuits in a darkened room is as follows:

1. Adjust the output of side detectors U1-1, U2-1 to approximately 440 mV.
2. Adjust the output of middle detector U1-7 to approx. 490 mV.
3. Adjust the reference potentiometer Vref. = 700 mV.

After adjustment, the output of the middle amplifier circuit is higher than that of the side ones. Without a reference circuit, the green LED would turn on. However the reference circuit will keep the output of the reference comparator at low state, logical "0" which will disable the output gate to the green LED (U7-13 at "0" state), until one of the detectors is exposed to laser light.

When one of the side detectors is exposed to laser light the amplifier output will be higher than that of the middle detector. When the middle detector is exposed, its output is higher than the reference voltage. A summary of the different illumination states is given in the following table, noting that VBIAS = 400 mV. All amplifiers are biased to 400 mVDC, and Vref. = 700 mV

| Det. Off (Dark) | | | Det. On (Illuminated) | | |
|---|---|---|---|---|---|
| Mid | Left/Dwn | Right/Up | Mid | Left/Dwn | Right/Up |
| 490 mV | 440 mV | 440 Mv | >1 V | 510 mV | 650 mV |

It can be seen from the table that when the middle detector is illuminated by the laser, its output voltage will be greater than VBIAS by a large margin (>1 V).

The crosshair test is accomplished by activating a large light field (30×30 cm) on the detector assembly 14 in such a way that the center of the crosshair is at isocenter (center of the ellipses 62 on the plate). When the crosshair shadow is exactly in the middle of the field, the shadow lines will cross over the middle slits 70 above the three staggered detectors on each side. This causes the output of the middle detector to drop below the side detectors, which are exposed to the light field. This results in turning off all the laser indicator lights on the display box. When the shadow is off the middle detector, the green light will go on, according to the table shown in FIG. 11.

The radiation field test is performed by using the sets 66 of seven staggered photodiodes located near the outer edge of the beam. The reference diode, which is mounted inside the field, is used in comparing its output, to the edge detectors. The size of the field (edge), is determined by the diode having an output which is smaller than fifty percent of the output of the reference diode.

The preamplifier's outputs are routed through the fifty pin edge connector and ribbon cable to the display panel 20. All circuits are adjusted to the same output level, when irradiated inside the field. The peak detector maintains the output voltage, which is the peak value of the pulse, with a time constant of $t = (R \times C) = 10^7 \times 0.3 \times 10^{-6} = 3$ sec.

As shown in FIGS. 12A–12L, there are seven comparators U14, U15 for each section (edge). Each diode output is compared to a reference diode output ($V_{ref}$ is adjusted to 0.5 Vmax.). If $V_{ref}$ is higher than the edge detector output, the comparator output is at a high state, logical "1"; if lower, the comparator output is at a low state, logical "0".

The purpose of the priority circuit is to determine and light the proper LED according to radiation field size. The outputs of comparators are at a low state for each detector that is in the radiation field and are greater than the reference voltage ($V_{ref}$). If the display was connected directly to the outputs of comparators, all LED's connected to the low state outputs would light up. However, the priority circuit (U17 and U18) converts the outputs of the comparators and generates signals to the display to turn on only the LED that corresponds to the outermost detector. LEDs corresponding to detectors totally within the radiation field will not turn on.

Figure 13:
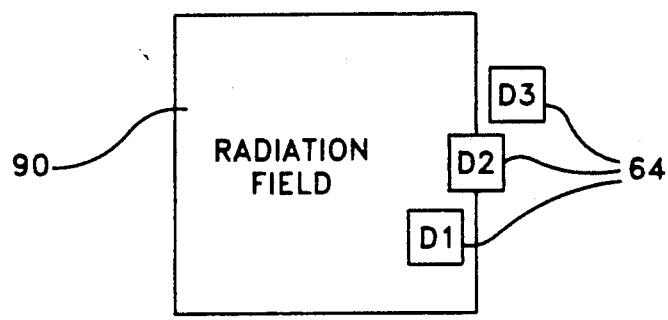
FIG. 13 is a schematical illustration of a radiation field and photodetectors positioned near the edge of the field.
Figure 14:
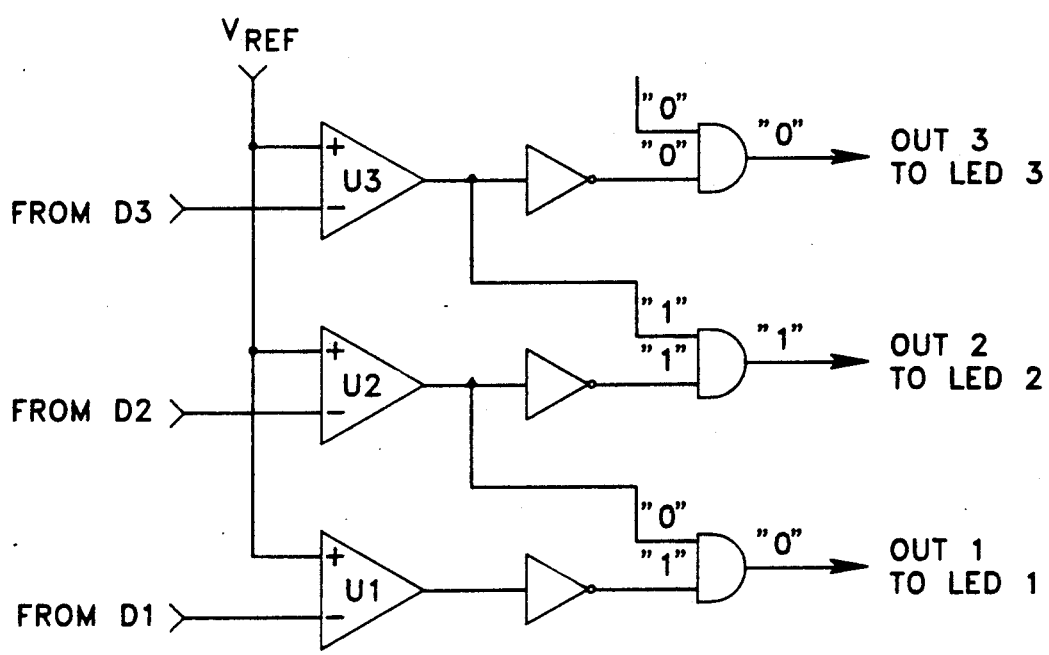
FIG. 14 is a schematical circuit diagram illustrating a priority circuit and logic used in determining radiation field size.

If, for example, the edge of the radiation field 90 pass through the middle detector, D2, as in FIG. 13, $V_{D1}$ and $V_{D2}$ will be greater than $V_{ref}$ (FIG. 15) and $V_{D3}$ smaller than $V_{ref}$. Outputs of comparators U1 and U2 will go low ("0"), and U3 high, "1". The priority circuit transforms these outputs to those shown in FIG. 14, so only LED 2, which is connected to output 2, (logical "1"), will light up to display the true edge of the field.

Figures 15, 17:
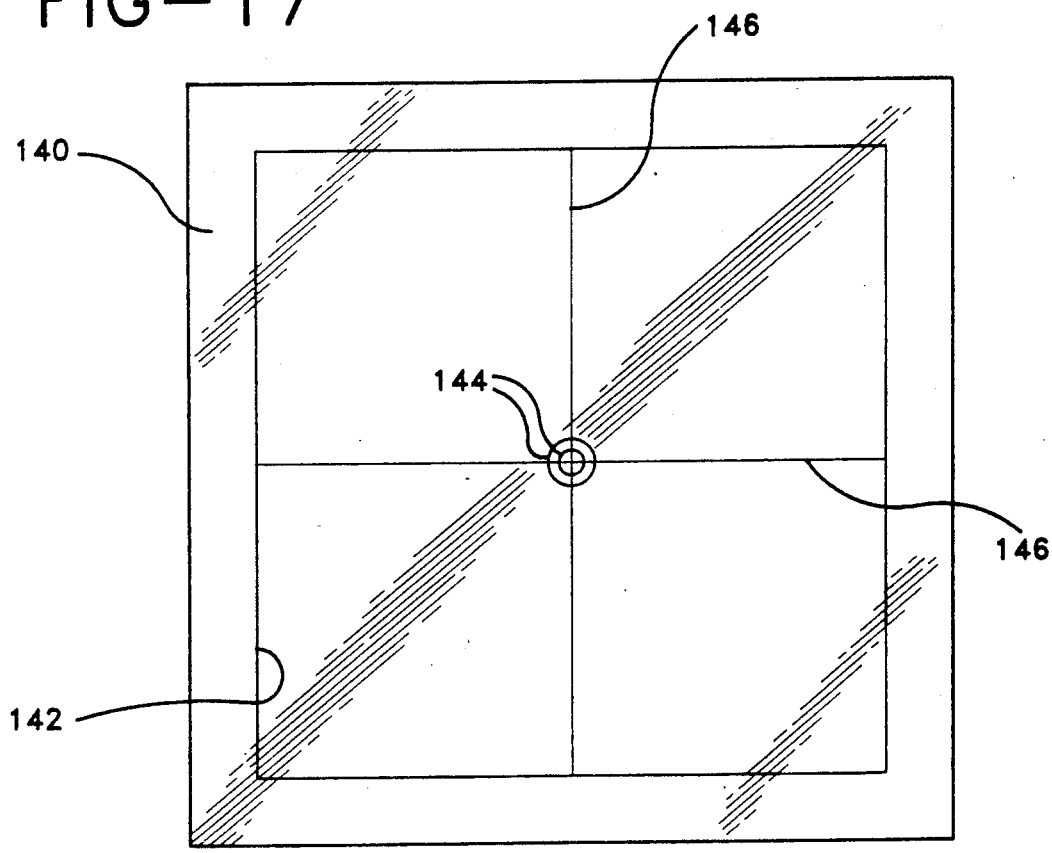
FIG. 15 is a truth table illustrating which light emitting diodes are illuminated upon illumination of various sets of photodetectors.
FIG. 17 is a top plan view of a phosphorescent screen and surface indicia used as a detector assembly.

The edge detection circuit shown in FIGS. 12A–12L includes two four bit latches, U19, U20, and a timing circuit, U15, U21, U16, U22, that generates the clock pulse to strobe and store the resulting edge information after irradiation. The display (7 LED's) is connected through 220 Ω resistors to the outputs. The information shown on the display will remain until a reset button is pressed to clear the latch. In the reset state, all LED's 78 are off. The relation between the display LED's lit, and photodiodes irradiated is described in the truth table (FIG. 15).

As discussed above, the display plate 20 includes of four sets 78 of bar graph LED's 79 for field size indication, and individual LEDs 76 for laser alignment (FIG. 7). For perfect laser alignment, the green light should be on. If a red light is on, the laser is misaligned by 0.5 mm to the side the light is on. For correct field size, the middle LED on the bar graph display 78 is on. Any deviation from the middle LED indicates an inaccuracy in field size with 0.5 mm resolution.

The video camera 16 and monitor 18 are conventional items and need not be described in great detail. As discussed above, the camera is aimed at the isocenter. It includes a telescopic lens which provides a magnified image of the isocenter and intersecting lines 72, 74. When the detector assembly is oriented at a forty-five degree angle from horizontal, the ellipses 62 appear as a set of circles upon the monitor. The use of a monitor eliminates problems due to parallax which would arise if the detector assembly were viewed directly.

The PIN silicon photodiodes 64 employed in the detector assembly can be used to detect both light and radiation. The relatively small active areas (2.71 mm × 2.71 mm) of the photodiodes in each set 66 allow high spacial resolution to be attained.

In use, the system 10 allows the user to check the light field of a therapeutic machine with its cross hair, gantry and collimator angle indictors and isocentricity. Laser positioning, radiation/light field coincidence testing and testing of the optical distance indicator may also be accomplished.

The cross hair test is conducted when a target shadow is generated upon the face of the detector assembly 14 while the detector assembly is oriented at about a forty-five degree angle with respect to the horizontal plane. Depending upon the orientation of the radiation head 38 with respect to the detector assembly, the perpendicular lines defining the target shadow intersect at or near the isocenter of the detector assembly. One of the lines passes through a first pair of the plates 68 while the other of the lines passes through the second pair of plates 68. If the shadow passes through the center slits 70 within the plates and through the isocenter, the appropriate indicator lights 76 in the display plate will remain unlit.

The radiation head and detector assembly are rotated the same number of degrees to a second rotational position, the head being rotated with the gantry. The center of the target shadow should remain within a small distance of the isocenter during such rotation. The position of the target shadow with respect to the isocenter is observed by viewing the monitor 18. The ellipses 62 appear as enlarged circles upon the monitor. If the center of the target shadow moves outside of a tolerance zone in one of the rotational positions of the radiation head, alignment is necessary. The collimator is checked in this manner at three gantry positions.

The alignment of the lasers 44 is checked by determining where the beams therefrom intersect the detector assembly 14. The beams should pass through the isocenter and the center slits 70 within the plates 68. Since this procedure is conducted in an otherwise unlit room, the center lights 76 of each set of indicator lights within the display plate 20 should be illuminated at this time. If not, the lasers should be properly aligned. Two lasers which provide a pair of orthogonal beams may be checked at the same time.

The radiation/light field coincidence test is conducted with the detector assembly oriented in a horizontal plane and substantially perpendicular with respect to the radiation head. An ordinary light beam from the head impinges upon the detector assembly. The detector assembly is positioned at such a distance from the light source that the "edges" of the light field created by the beam are defined in the general areas of the four sets 66 of photodiodes 64. The center diode 64 beneath the ellipses 62 should receive the highest intensity radiation.

The center photodiode 64 is used for normalization. The peak output from this photodiode is detected. Since the intensity of the light steadily decreases in the areas defined by the four sets 66 of photodiodes, the peak output of any of the photodiodes comprising the respective sets should be equal to or less than fifty percent of the center photodiode. The peak outputs of these photodiodes are compared to the peak output of the center photodiode as described above. Four LED's 79 corresponding to the photodiodes 64 at the edge of the light field will be illuminated.

The source of ordinary light is turned off once the light field is properly centered upon the detector assembly and the "edges" of the light field have been determined in the above-described manner. The detector assembly is then exposed to the radiation field, and a similar analysis conducted. The light emitting diodes 79 illuminated during this procedure should be substantially the same ones which were illuminated when the ordinary light field was generated. If not, the radiation and light fields are not coincident, and appropriate adjustments must be made.

Figure 16:
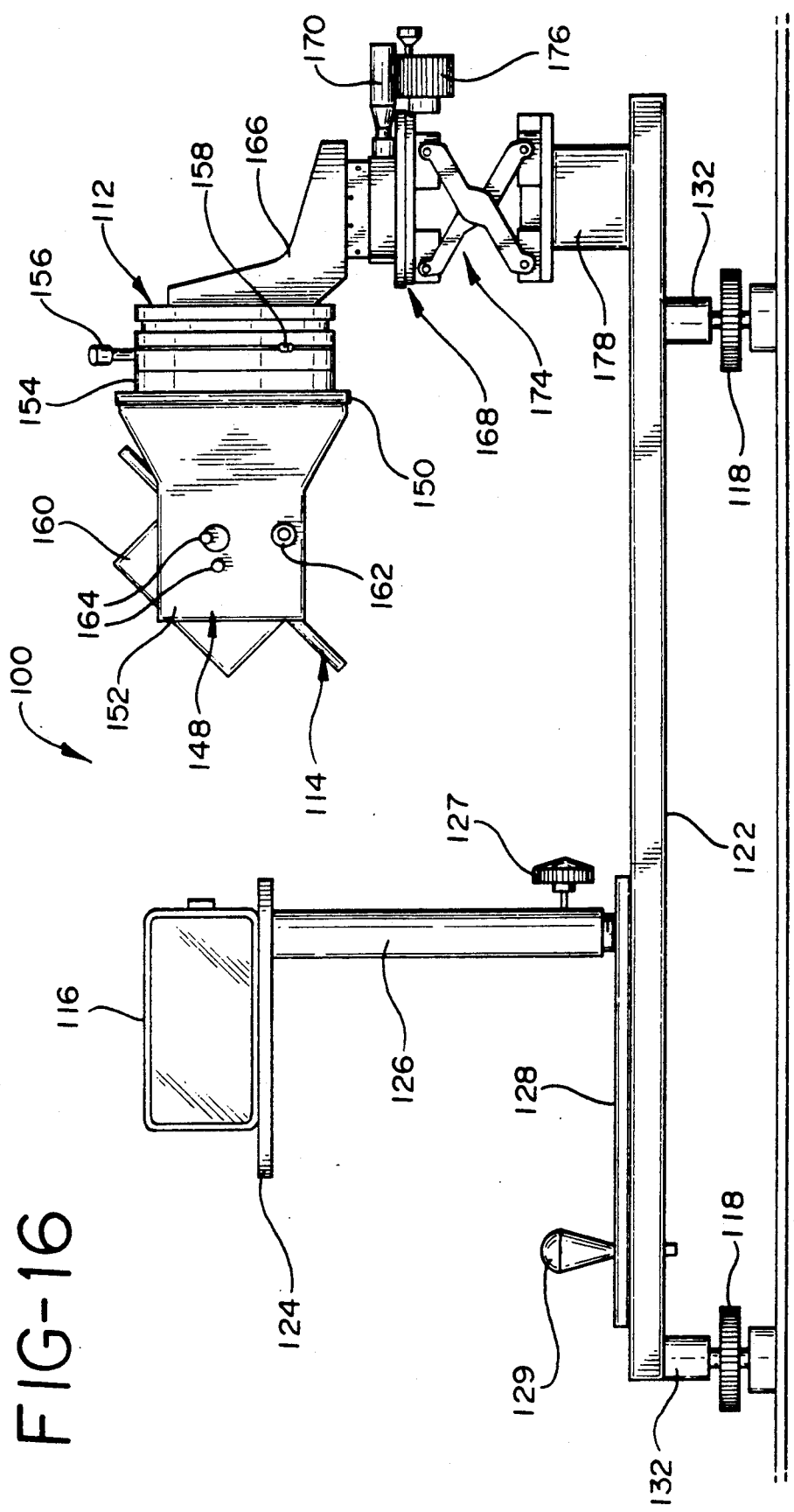
FIG. 16 is a side elevation view of an alternative embodiment of the invention.

A second embodiment of the invention is shown in FIG. 16. A system 100 is provided which, like the system 10 discussed above combines into a single instrument the multiple functions which are necessary for quality control of teleradiotherapy machines such as high energy accelerators, Co-60 machines, and low energy x-ray machines.

The system 100 includes a rotary stage 112, a detector assembly 114 supported by the rotary stage, and a video camera 116.

The rotary stage 112 and camera 116 are both supported by a base 122 which is adjustable in height by turning the adjustment screws 118 of the base legs 132. The camera 116 is positioned upon a platform 124 which is maintained parallel with respect to the above-referenced base by a vertical column 126. The height of the column 126 may be adjusted by an adjustment screw 127. A second platform 128 supports the column 126. The second platform 128 may be moved towards or away from the detector assembly 114 unless locked in place by a locking member 129 which extends through both the second platform 128 and the base.

The detector assembly 114 is a phosphorescent screen 140, as best shown in FIG. 17. A trapezoidal border 142, a pair of concentric ellipses 144 and a pair of orthogonal lines 146 are provided upon the substantially planar surface of the screen. The border is preferably, but not necessarily contiguous. The lines 146 intersect at the isocenter of the detector assembly 114.

The detector assembly is supported by a mounting bracket 148 including a backplate 150 and a pair of parallel arms 152 extending from the backplate 150. The backplate is secured to a rotatable ring 154 of the rotary stage 112. Set screws 156,158 are provided on the rotary stage for fine tuning the rotational position of the ring 154 and locking it in any rotational position, respectively. The detector assembly 114 may accordingly be rotated about the y axis, i.e., the axis of rotation of the gantry.

A pair of opposing walls 160 are secured to the screen 140. These walls 160 are pivotably secured to the opposing arms 152 of the mounting bracket by a pair of pivot pins 162. Corresponding holes within the opposing arms 152 and walls 160 allow the screen to be fixed by a pin at a 45° angle, as shown, or in the horizontal position. The holes in the arms 152 are designated by numeral 164.

A generally L-shaped bracket 166 secures the rotary stage 112 to a support 168 which allows the height and horizontal position of the detector assembly to be adjusted. An adjustment screw 170 is provided for moving the bracket 166 with respect to a plate-like base 172 along an axis parallel to the y axis. The base 172 is mounted to a translational stage 174, the height of which is adjustable by rotating a wheel 176 operatively associated therewith. The translational stage 174 is mounted to a block 178 which is affixed to the base 122.

The phosphorescent screen 140 should be reactive to the wavelengths of radiation it receives from the radiotherapy machine. A relatively intense reaction is preferred. The detector assembly 114, which includes no photodiodes such as those employed in the first-mentioned detector assembly 14, is used in a different manner to conduct the various tests of radiotherapy machines. As discussed above, such tests include tests of the light fields (position, size), isocentricity of the gantry and collimator, patient positioning lasers, and coincidence of the radiation and light fields.

Preliminary to conducting any tests, the detector assembly 14 is positioned directly beneath the collimator and oriented at a forty-five degree angle. The cross hair shadow is aligned with the intersecting lines 146 on the upper surface of the screen 140. Using the optical distance indicator which is incorporated within most radiation therapy machines, the operator verifies that the source to surface distance (SSD) is one hundred centimeters.

The isocentricity of the gantry and collimator are checked by observing the positions of the center of the cross hair with respect to the ellipses 144 at various rotational positions of the gantry, collimator, and screen, respectively. The center of the cross hair should remain within a selected distance of the isocenter of the screen 140, as measured by the ellipses 144, at all positions of the gantry and collimator. The use of a monitor 18, as shown in FIG. 1, facilitates the procedure as an enlarged view of the screen 140 is provided by the video camera 116.

Laser alignment is conducted by orienting the screen to receive the beams from the lasers positioned about the room. Several rotational positions are required to check all of the lasers in a typical room used for therapy. Two lasers are checked at the same time, each of which produces an illuminated line upon the screen 140 which should be coincident with one of the two orthogonal lines 146.

Coincidence of the light and radiation fields is checked by first observing the edge of the light field with respect to the border 142. They should be coincident. The operator then leaves the room and actuates the radiotherapy machine. The screen is caused to glow in response to the radiation, causing a radiation field to be illuminated. This field, like the light field, should have a peripheral edge which is substantially coincident with the border 142. The operator is able to determine the coincidence of the light and radiation fields outside the therapy room by observing the screen 140 on a monitor.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An assembly for testing the alignment of a radiation source, comprising:
   a mounting fixture;
   a detector assembly mounted to said mounting fixture, said detector assembly including an isocenter and radiation detection means responsive to radiation, said mounting fixture including means for supporting said detector assembly in such a manner that said detector assembly is rotatable about first and second axes, said first and second axes being arranged such that the isocentricity of the detector assembly is maintained in substantially all rotational positions about each of said axes.

2. An assembly as defined in claim 1 wherein said first axis is substantially perpendicular to said second axis, each of said axes being in a horizontal plane.

3. An assembly as defined in claim 1 including a camera aimed at the isocenter of said detector assembly.

4. An assembly as defined in claim 3 including means for displaying an image detected by said camera.

5. An assembly as defined in claim 1 wherein said radiation detection means include photodiodes.

6. An assembly as defined in claim 1 wherein said radiation detection means include a luminescent screen.

7. An assembly as defined in claim 1 wherein said radiation detection means include means for detecting radiation impinging upon a plurality of discrete points upon said detector assembly, and display means for displaying whether one or more of said discrete points are irradiated.

8. An assembly as defined in claim 1 wherein said radiation detection means include a plurality of discrete sets of radiation detectors, each of said sets being substantially equidistant from said isocenter.

9. An assembly as defined in claim 1 wherein said detector assembly includes means for detecting the location of an edge of a field of radiation generated thereon.

10. An assembly as defined in claim 9 wherein said means for detecting an edge of a field of radiation include a substantially planar surface and a substantially rectangular border marked upon said surface.

11. An assembly as defined in claim 9 wherein said means for detecting an edge of a field of radiation include a plurality of photodetectors.

12. An assembly as defined in claim 9 wherein said detector assembly includes means for detecting whether a target shadow line passes over a preselected line defined upon said detector assembly.

13. An assembly as defined in claim 12 wherein said detector assembly includes means for detecting whether a second target shadow line passes over a second preselected line defined upon said detector assembly.

14. An assembly as defined in claim 9 wherein said detector assembly includes means for detecting whether a first line of radiation passes over a preselected line defined upon said detector assembly.

15. An assembly as defined in claim 14 wherein said detector assembly includes means for detecting whether a second line of radiation passes over a second preselected line defined upon said detector assembly.

16. An assembly as defined in claim 1 including calibration means for determining the rotational position of said detector assembly with respect to at least one of said first and second axes.

17. An assembly as defined in claim 1 including a target defined at the isocenter of said detector assembly.

18. An assembly as defined in claim 17 wherein said target includes a plurality of concentric ellipses.

19. An assembly as defined in claim 1 including means for comparing the intensity of radiation near the edges of a radiation field upon said detector assembly with the intensity of radiation within the field.

20. An assembly as defined in claim 1 wherein said detector assembly includes a substantially planar surface, said surface including markings which define a substantially rectangular border, the isocenter of said detector assembly, and a pair of orthogonal lines.

21. An assembly as defined in claim 1 including means for adjusting the height of said detector assembly.

22. An assembly as defined in claim 1 wherein said detector assembly includes means for detecting whether a target shadow line passes over a preselected line defined upon said detector assembly.

23. An assembly as defined in claim 22 wherein said detector assembly includes means for detecting whether a second target shadow line passes over a second preselected line defined upon said detector assembly.

24. An assembly as defined in claim 1 wherein said detector assembly includes means for detecting whether a first line of radiation passes over a preselected line defined upon said detector assembly.

25. An assembly as defined in claim 24 wherein said detector assembly includes means for detecting whether a second line of radiation passes over a second preselected line defined upon said detector assembly.

26. An assembly as defined in claim 24 wherein said preselected line is defined by a pair of photodetectors.

27. An assembly as defined in claim 24 wherein said preselected line is defined by a line marked upon said detector assembly.

28. An assembly as defined in claim 9 including a target defined upon said detector assembly, said target being positioned at the isocenter thereof.

29. An assembly as defined in claim 28 wherein said target includes a plurality of concentric ellipses.

30. An assembly as defined in claim 1 wherein said mounting fixture includes a rotary stage, a bracket mounted to said rotary stage, said detector assembly being pivotably mounted to said bracket.

31. An assembly for testing the alignment of a radiation therapy machine, comprising:
   a mounting fixture;
   a detector assembly mounted to said mounting fixture, said detector assembly including a substantially planar surface;
   a border, a pair of orthogonal lines, and a target marked upon said substantially planar surface; and
   means for supporting said detector assembly upon said mounting fixture in such a manner that said detector assembly is rotatable about first and second axes, said first and second axes being arranged such that the isocentricity of the detector assembly is maintained in substantially all rotational positions about each of said axes, the isocenter of said detector assembly being defined by said target.

32. An assembly as defined in claim 31 including a camera aimed at said substantially planar surface of said detector assembly.

33. An assembly as described in claim 32 including a monitor connected to said camera.

34. An assembly as described in claim 33 wherein said substantially planar surface includes a phosphorescent screen.

35. An assembly as described in claim 31 including means for adjusting the height of said detector assembly.

36. An assembly as described in claim 31 wherein each of said orthogonal lines is aligned with said target.

37. An assembly as described in claim 31 wherein said target includes at least one ellipse.

38. A method of checking the alignment of a radiation head rotatably mounted to a gantry, said radiation head including means for generating a target shadow, comprising the steps of:

providing a detector assembly and means for rotating said detector assembly about at least two substantially perpendicular axes while maintaining the isocentricity of said detector assembly, said detector assembly including a target at the isocenter thereof;

positioning said detector assembly in a first rotational position in opposing relation t said radiation head while said gantry is in a first rotational position;

causing said radiation head to generate a target shadow such that said target shadow appears upon said target;

rotating said gantry a selected number of degrees about a horizontal axis to a second rotational position;

rotating said detector assembly said selected number of degrees about an axis to a second rotational position such that said detector assembly remains in opposing relation to said radiation head; and observing the position of said target shadow with respect to said target in said second rotational position.

39. A method as defined in claim 38 wherein said target includes a plurality of substantially concentric ellipses, including the step of orienting said detector assembly at a non-perpendicular angle with respect to said radiation head.

40. A method as defined in claim 38 including the step of rotating said radiation head about a second axis orthogonal to said horizontal axis, and observing the position of said target shadow with respect to said target subsequent to rotating said radiation head.

41. A method of determining the edge of a non-ionizing light or an ionizing radiation field generated by a radiation therapy machine, comprising:

providing a detector assembly including a substantially flat, luminescent surface and a border marked upon said surface;

causing said radiation therapy machine to sequentially generate non-ionizing light and ionizing radiation fields upon said substantially flat surface; and observing the peripheral edges of the respective fields and the luminescence of said surface with respect to the border.

42. A method as described in claim 41 wherein said border is substantially trapezoidal.

* * * * *